US010610613B2

(12) United States Patent
Ota et al.

(10) Patent No.: US 10,610,613 B2
(45) Date of Patent: Apr. 7, 2020

(54) ABSORBENT ARTICLE COMPRISING WATER-ABSORBENT RESIN POWDER

(71) Applicant: LIVEDO CORPORATION, Shikokuchuo-shi, Ehime (JP)

(72) Inventors: Yoshihisa Ota, Tokushima (JP); Emi Amano, Tokushima (JP)

(73) Assignee: LIVEDO CORPORATION, Shikokuchuo-shi (JP)

(*) Notice: Subject to any disclaimer, the term of this patent is extended or adjusted under 35 U.S.C. 154(b) by 458 days.

(21) Appl. No.: 14/391,051

(22) PCT Filed: Apr. 25, 2013

(86) PCT No.: PCT/JP2013/002810
§ 371 (c)(1),
(2) Date: Oct. 7, 2014

(87) PCT Pub. No.: WO2013/161306
PCT Pub. Date: Oct. 31, 2013

(65) Prior Publication Data
US 2015/0065980 A1 Mar. 5, 2015

(30) Foreign Application Priority Data

Apr. 26, 2012 (JP) .................... 2012-100809

(51) Int. Cl.
*A61F 13/15* (2006.01)
*A61L 15/24* (2006.01)
(Continued)

(52) U.S. Cl.
CPC ............ *A61L 15/24* (2013.01); *A61F 13/496* (2013.01); *A61F 13/53* (2013.01); *A61F 13/537* (2013.01); *A61L 15/60* (2013.01)

(58) Field of Classification Search
CPC ....... A61F 13/5323; A61L 15/42; A61L 15/60
See application file for complete search history.

(56) References Cited

U.S. PATENT DOCUMENTS 5,621,055 A 4/1997 Miyanaga et al.
5,668,078 A 9/1997 Sumiya et al.
(Continued)

FOREIGN PATENT DOCUMENTS

AU 25757/95 A 1/1996
EP 0 586 976 A1 3/1994
(Continued)

OTHER PUBLICATIONS

Buchholz et al., "Modern Superabsorbent Polymer Technology", John Wiley & Sons, Inc., (1998), (24 pages).
(Continued)

*Primary Examiner* — Michele M Kidwell
(74) *Attorney, Agent, or Firm* — Westerman, Hattori, Daniels & Adrian, LLP

(57) ABSTRACT

To provide an outer absorbent article having attached thereto an inner absorbent article such as a urine absorption pad to be used, in which the outer absorbent article is configured to prevent inside thereof from wetting due to condensation of vapor escaped from inside an inner absorbent article. [Solution] An outer absorbent article of the present invention is an outer absorbent article having an absorbent body formed from at least one layer of an absorption layer, wherein the absorbent body includes a water-absorbent resin powder satisfying the following requirements of (a) to (d). (a) Specific surface area measured by BET multipoint method: 0.040 $m^2$/g to 0.200 $m^2$/g (b) Vapor blocking ratio: 0% to 0.90% (c) Absorption ratio: 30 g/g to 70 g/g (d) Water retention amount: 45 g/g to 60 g/g.

20 Claims, 11 Drawing Sheets

(51) Int. Cl.
*A61F 13/537* (2006.01)
*A61L 15/60* (2006.01)
*A61F 13/496* (2006.01)
*A61F 13/53* (2006.01)
*A61F 13/20* (2006.01)

(56) References Cited

U.S. PATENT DOCUMENTS

| | | | |
|---|---|---|---|
| 6,124,391 | A | 9/2000 | Sun et al. |
| 6,184,433 | B1 | 2/2001 | Harada et al. |
| 6,562,879 | B1 | 5/2003 | Hatsuda et al. |
| 8,388,585 | B2 * | 3/2013 | Tomes .................. A61F 13/15 604/329 |
| 2003/0153887 | A1 | 8/2003 | Nawata et al. |
| 2006/0184146 | A1 | 8/2006 | Suzuki |
| 2007/0038196 | A1 | 2/2007 | Karlsson et al. |
| 2007/0178786 | A1 | 8/2007 | Nawata et al. |
| 2009/0136736 | A1 | 5/2009 | Nawata et al. |
| 2010/0273647 | A1 | 10/2010 | Nawata et al. |
| 2013/0175473 | A1 | 7/2013 | Wada et al. |

FOREIGN PATENT DOCUMENTS

| | | | |
|---|---|---|---|
| EP | 0 872 491 | A1 | 10/1998 |
| EP | 1 029 886 | A2 | 8/2000 |
| EP | 1 291 368 | A1 | 3/2003 |
| EP | 1291368 | A1 * | 3/2003 |
| EP | 1 609 448 | A1 | 12/2005 |
| JP | 2003-93440 | A | 4/2003 |
| JP | 2005-95759 | A | 4/2005 |
| JP | 2009-35657 | A | 2/2009 |
| JP | 2011-45609 | A | 3/2011 |
| JP | 2011-182906 | A | 9/2011 |
| JP | 2011-182907 | A | 9/2011 |
| JP | 2012-7062 | A | 1/2012 |
| WO | 95/33558 | A1 | 12/1995 |
| WO | 2005/092955 | A1 * | 10/2005 |
| WO | 2012/043821 | A1 | 4/2012 |

OTHER PUBLICATIONS

Office Action dated Feb. 9, 2016, issued in counterpart Japanese Patent Application No. 2012-100809, with English translation. (6 pages).
Office Action dated Mar. 16, 2016, issued in counterpart European Application No. 13725489.2 (5 pages).
Third Party Observation submitted Apr. 24, 2014 issued in corresponding Japanese application No. 2012-100809, (6 pages).
International Search Report with the Written Opinion dated Aug. 13, 2013, issued in corresponding application No. PCT/JP2013/002810.
Third Party Observations dated Aug. 26, 2014, issued in corresponding application No. PCT/JP2013/002810.

* cited by examiner

[Fig. 1]
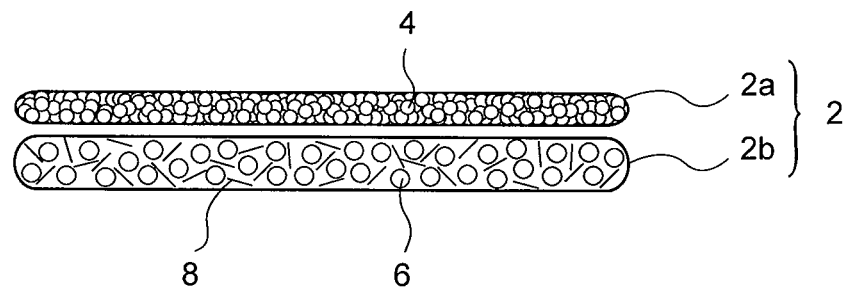
[Fig. 2]
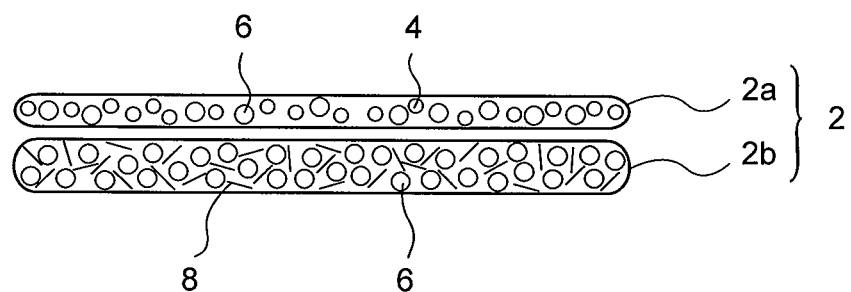
[Fig. 3]
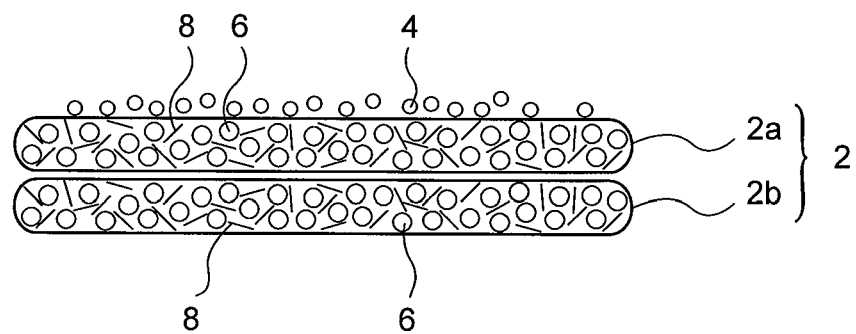

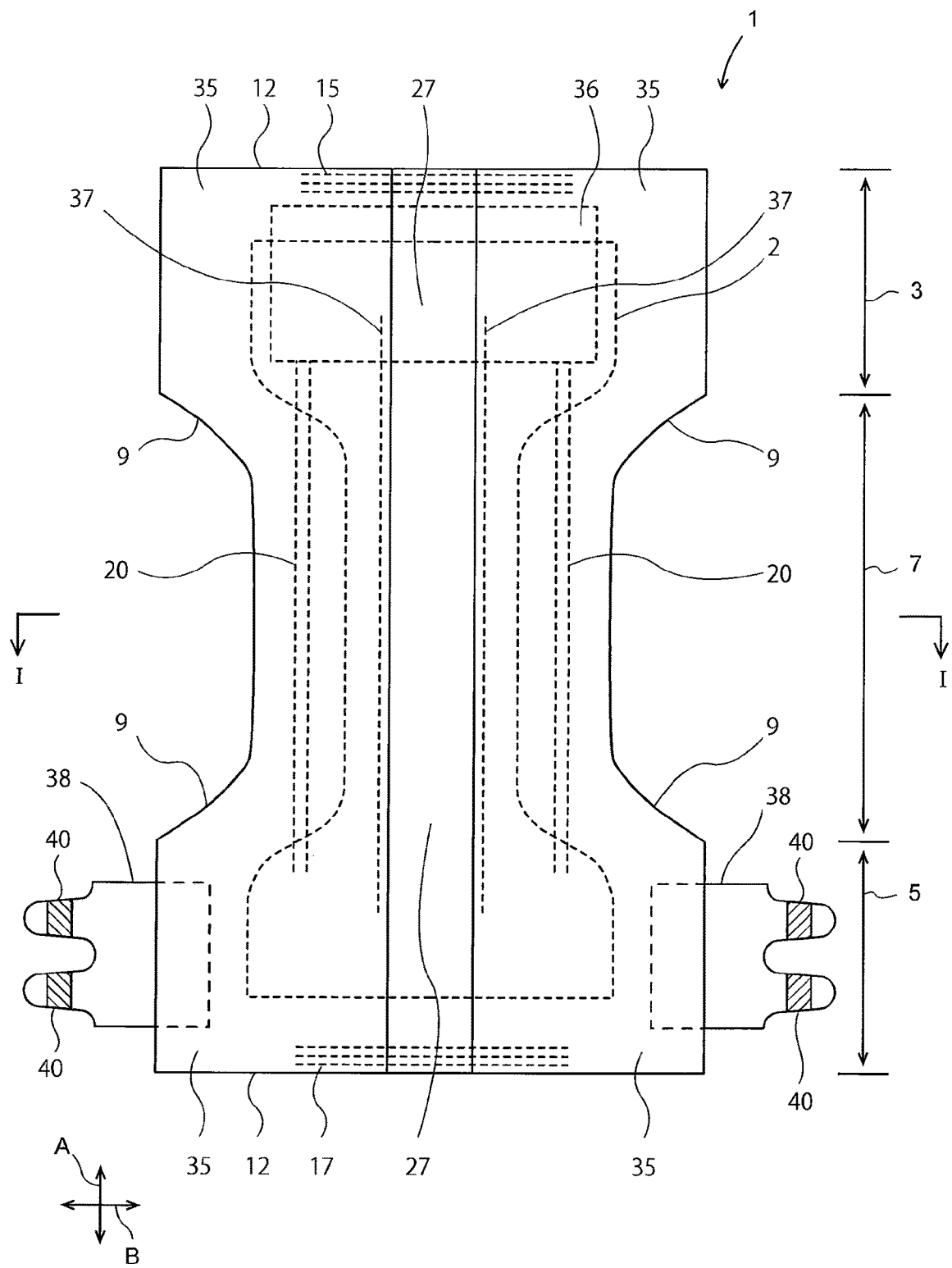
[Fig. 4]

[Fig. 5]
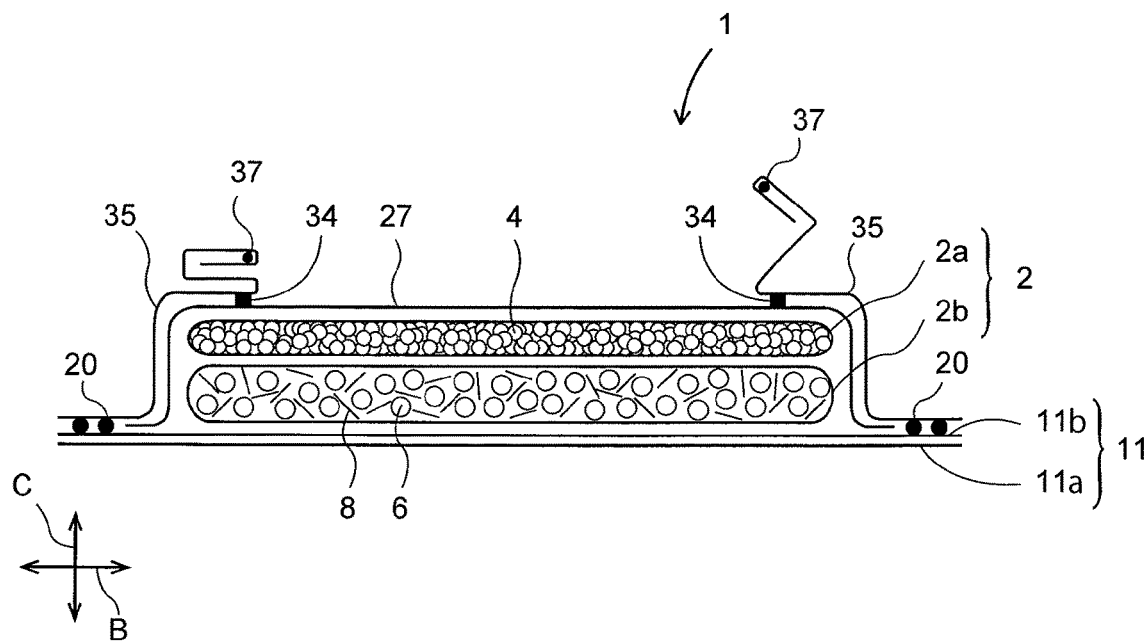

[Fig. 6]
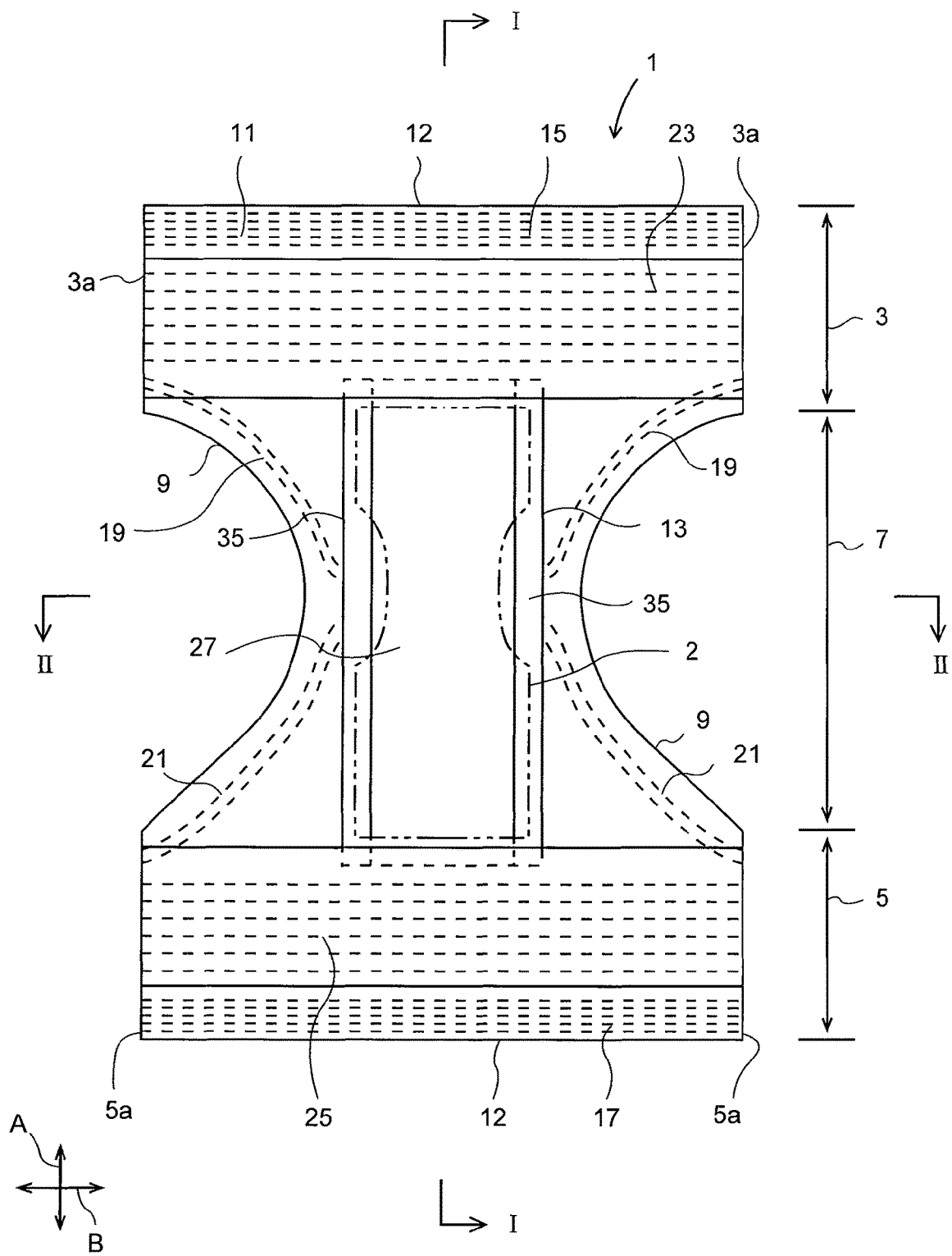

[Fig. 7]
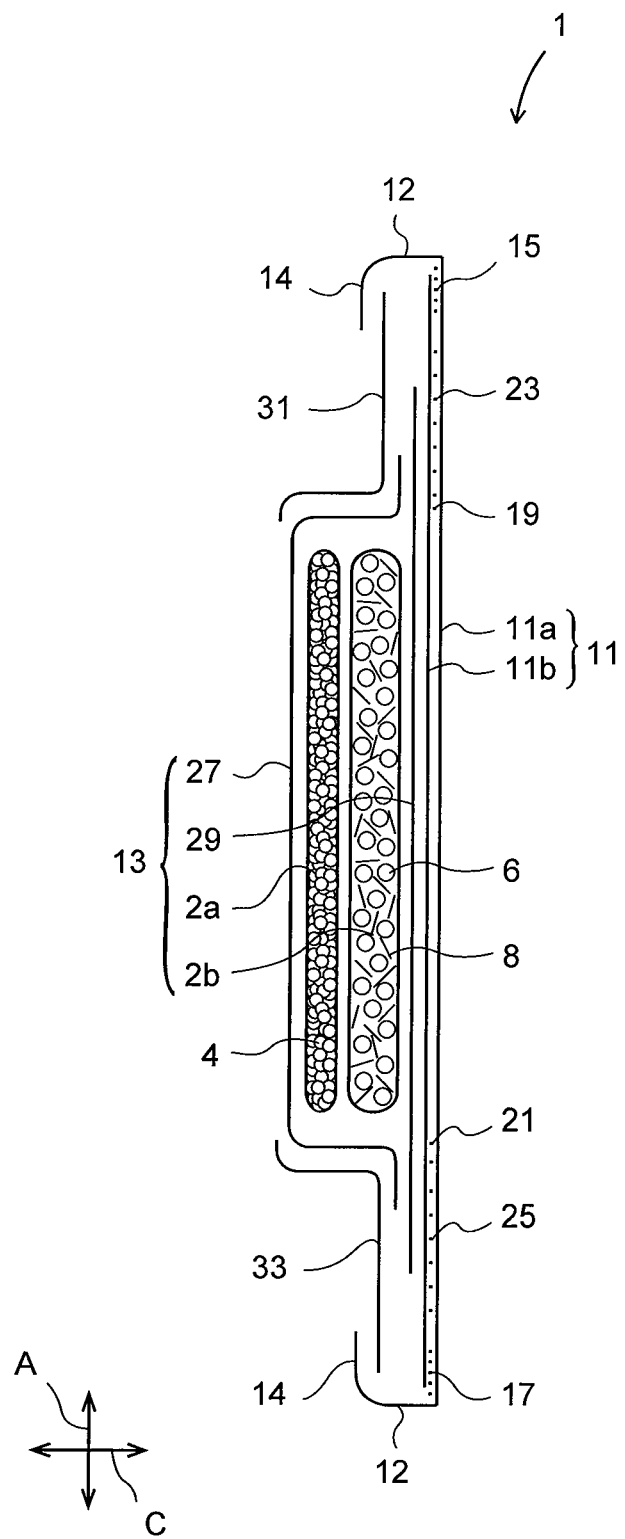

[Fig. 8]
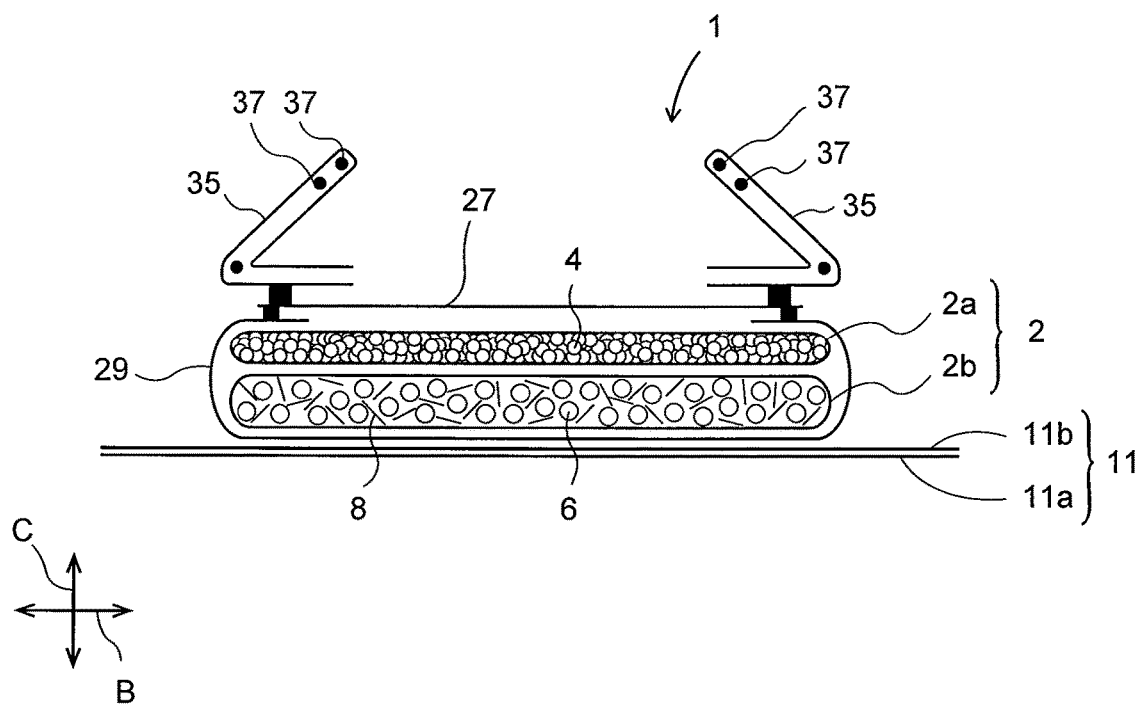

[Fig. 9]
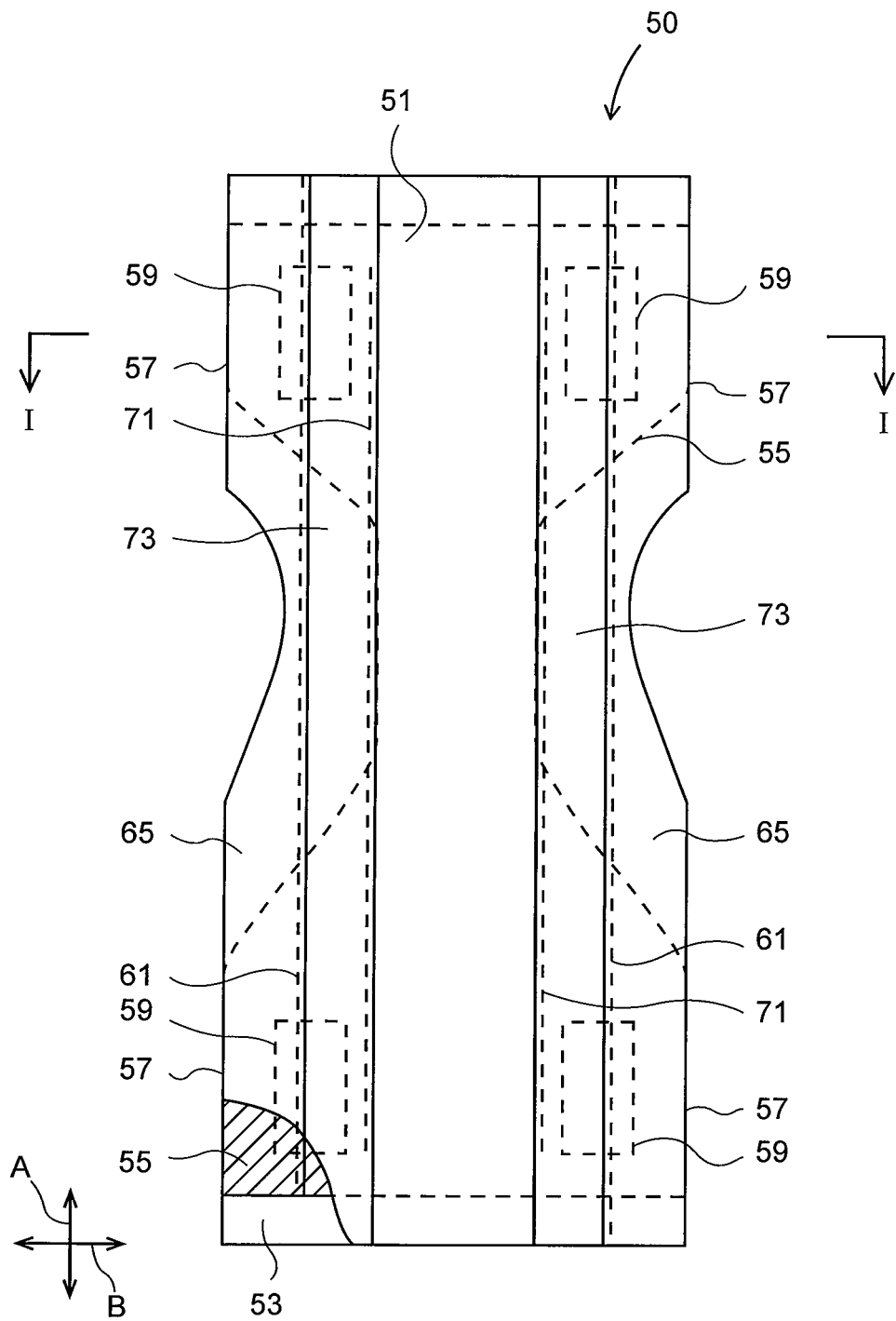

[Fig. 10]
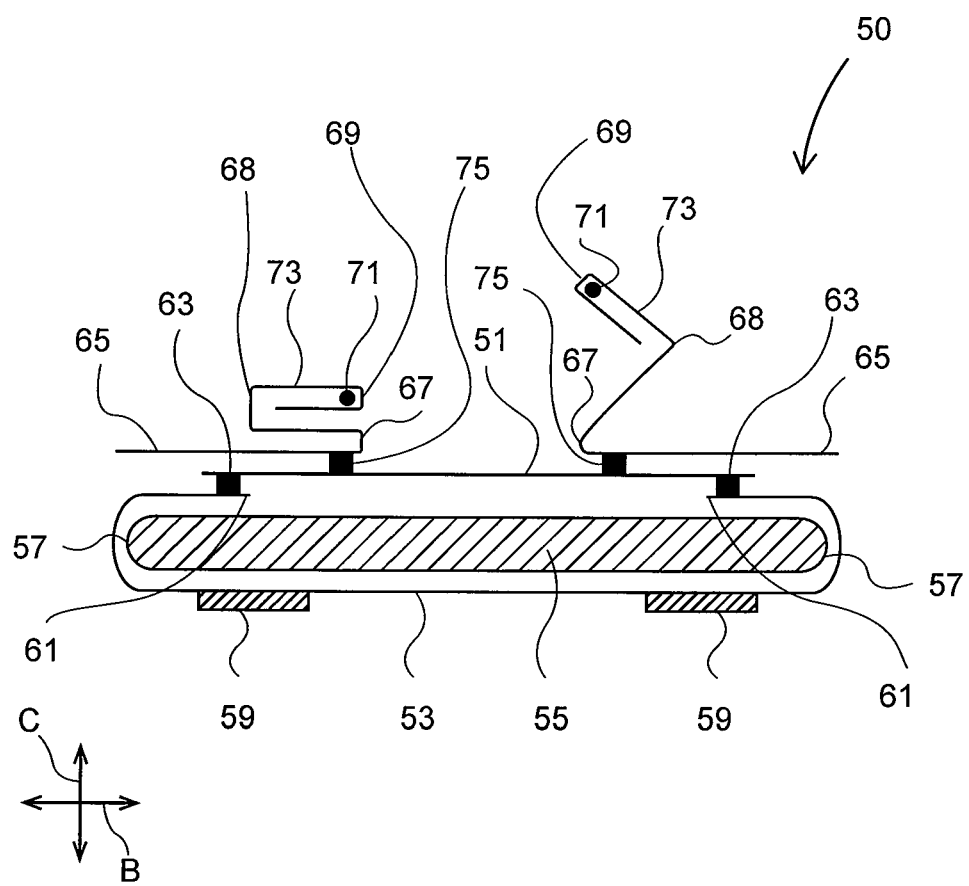

[Fig. 11]
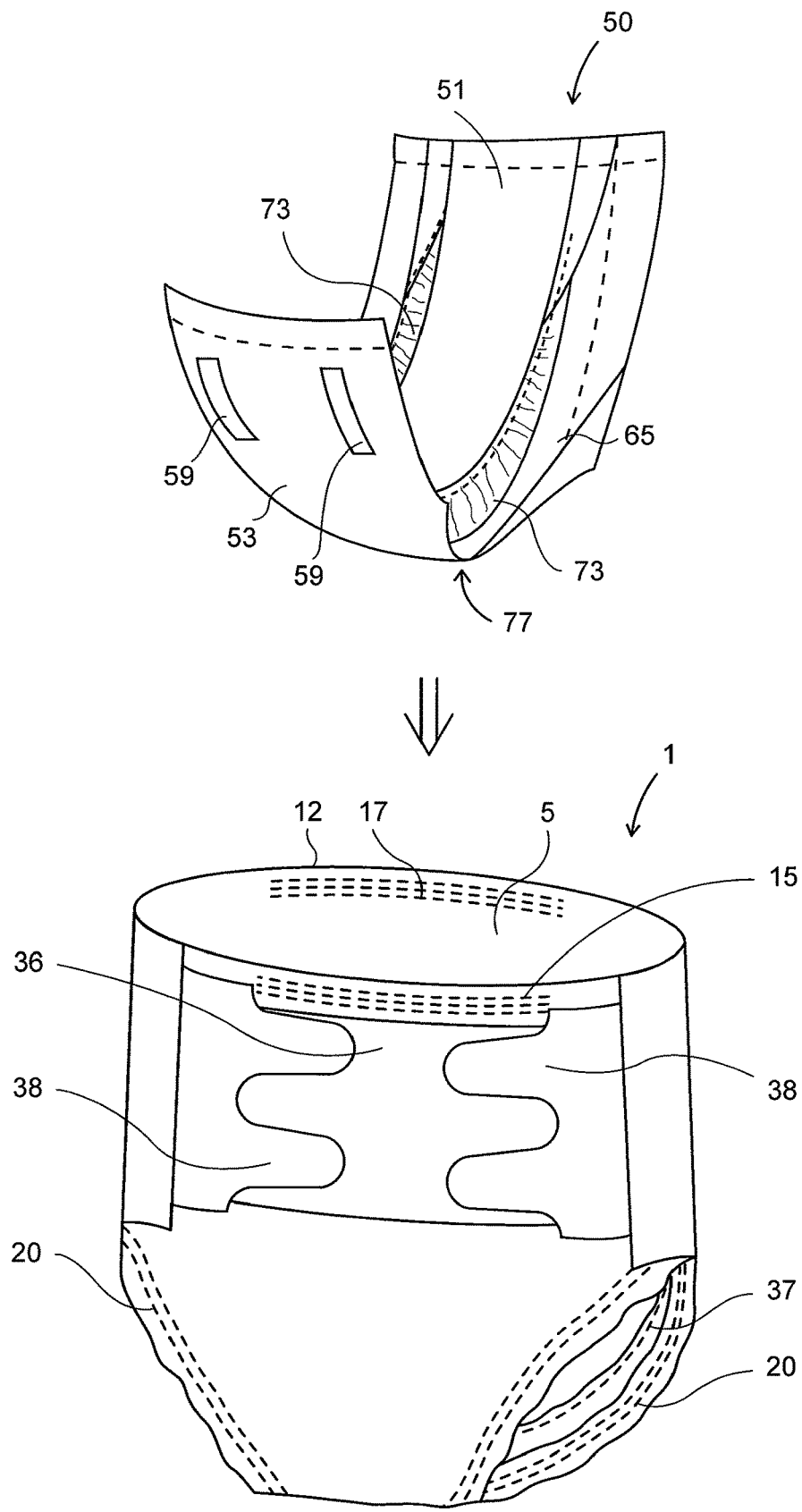

[Fig. 12]
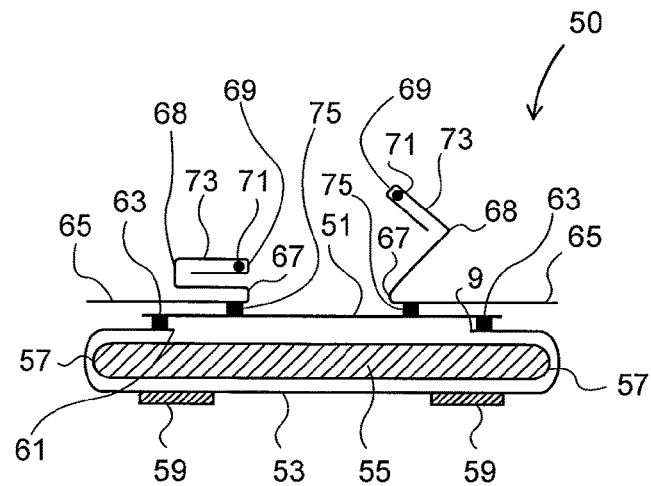
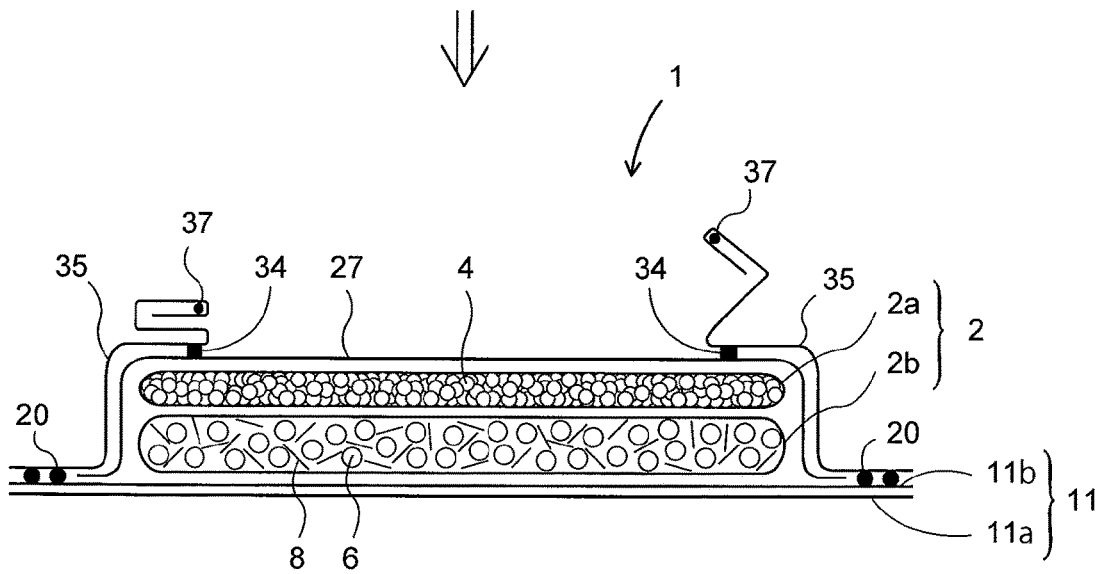
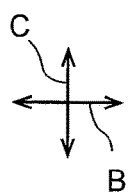

[Fig. 13]
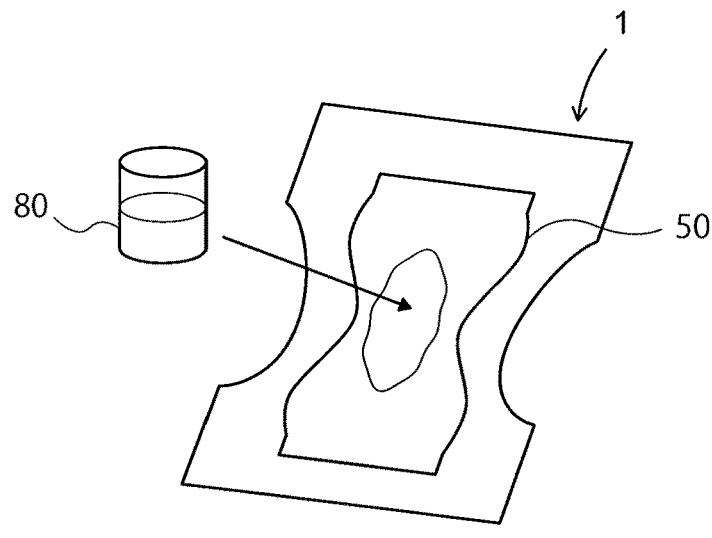
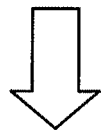
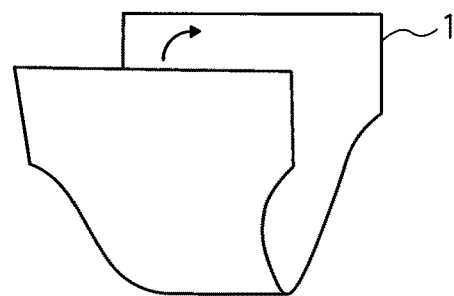
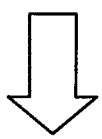
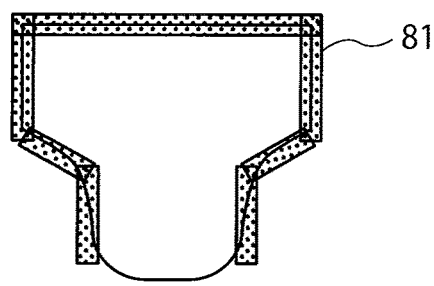

ABSORBENT ARTICLE COMPRISING WATER-ABSORBENT RESIN POWDER

TECHNICAL FIELD

The present invention relates to a technique for improving condensation on absorbent articles.

BACKGROUND ART

As absorbent articles represented by disposable diapers, there are known absorbent articles in which an inner absorbent article such as a urine absorption pad is attached to an outer absorbent article such as a diaper outer body. These absorbent articles are used mainly as disposable diapers for adults. When body fluid such as urine is excreted, an inner absorbent article absorbs the body fluid. Body fluid that cannot be absorbed by the inner absorbent article is absorbed by the outer absorbent article. In particular, when urination volume is not so large and the body fluid can be absorbed by the inner absorbent article alone, only the inner absorbent article can be replaced. Since the outer absorbent article may be replaced where necessary, this type of absorbent article is cost effective. In addition, the effort for nursing care is also reduced.

Generally, an outer sheet of such inner absorbent article has breathability in order to prevent dampness. Therefore, there has been a problem where vapor escaped from inside the inner absorbent article forms condensation on the inner surface of the outer absorbent article to wet the outer absorbent article. In such a case, the outer absorbent article needs to be replaced even if excrement such as urine has not attached thereto due to deterioration in the feel of wearing the absorbent article.

Absorbent articles that solve the above described problem are disclosed in, for example Patent Literatures 1 and 2. Patent Literature 1 discloses an absorbent article, which is applied on a region including a crotch portion of a wearer. The absorbent article includes: an absorption core for absorbing moisture; an inner sheet member disposed on a skin surface side of the absorption core and having at least a portion that is water permeable; and an outer sheet member disposed on an external surface side of the absorption core. The outer sheet member includes a porous resin film having breathability and waterproofness, and a water absorbent sheet having breathability and water absorptivity and laminated on an external surface side of the porous resin film.

Patent Literature 2 discloses a urine absorption pad, which is applied on a region including a crotch portion of a wearer. The urine absorption pad includes: an absorption core for absorbing moisture; an inner sheet member disposed on a skin surface side of the absorption core and having at least a portion that is water permeable; and an outer sheet member disposed on an external surface side of the absorption core. The outer sheet includes a porous resin film having breathability and waterproofness, an exterior sheet having breathability and laminated on an external surface side of the porous resin film, and an adhesive mixed with a water absorbent polymer and applied between the porous resin film and the exterior sheet to bond the porous resin film and the exterior sheet.

CITATION LIST

Patent Literature

PTL 1: Japanese Patent Publication No. 2011-182906
PTL 2: Japanese Patent Publication No. 2011-182907

SUMMARY OF INVENTION

Technical Problem

Although the inventions of Patent Literatures 1 and 2 both improve the inner absorbent article to prevent vapor from condensing inside the outer absorbent article, it is necessary to prevent vapor from condensing inside the outer absorbent article even when inner absorbent articles other than those described above are used. The present invention is made in view of the above described circumstances, and an object of the present invention is to provide an outer absorbent article that prevents the inner side thereof from being wet due to condensation of vapor escaped from within the inner absorbent article, without sacrificing absorption performance that is required funda-mentally, in an outer absorbent article to which an inner absorbent article such as a urine absorption pad is attached for use.

Solution to Problem

An outer absorbent article of the present invention is an outer absorbent article having an absorbent body composed of at least one absorption layer, wherein the absorbent body includes a water-absorbent resin powder satisfying following requirements of (a) to (d).

(a) Specific surface area measured by BET multipoint method: $0.040 \text{ m}^2/\text{g}$ to $0.200 \text{ m}^2/\text{g}$
(b) Vapor blocking rate: 0% to 0.90%
(c) Absorption ratio: 30 g/g to 70 g/g
(d) Water retention amount: 20 g/g to 60 g/g The water-absorbent resin powder satisfying the above described requirements of (a) to (d) has high vapor absorption performance. The absorbent body having such water-absorbent resin powder absorbs vapor inside the outer absorbent article. Therefore, the condensation of the vapor inside the outer absorbent article is suppressed. In addition, the water-absorbent resin powder satisfying the above described requirements of (a) to (d) has a low vapor blocking rate. Since blocking does not occur even when vapor is absorbed by the water-absorbent resin powder, the deterioration of the water absorption performance due to the blocking is suppressed. Furthermore, since the water-absorbent resin powder has constant water absorption performance, the water-absorbent resin powder is excellent in absorbing body fluid such as urine.

Advantageous Effects of Invention

According to the present invention, it is possible to suppress the condensation of vapor inside the outer absorbent article, regardless of the type of the inner absorbent article to be used.

BRIEF DESCRIPTION OF DRAWINGS

FIG. 1 is a schematic sectional view showing one example of an absorbent body of an outer absorbent article of the present invention.

FIG. 2 is a schematic sectional view showing one example of the absorbent body of the outer absorbent article of the present invention.

FIG. 3 is a schematic sectional view showing one example of the absorbent body of the outer absorbent article of the present invention.

FIG. 4 is a plan view (expansion plan) of one example of the outer absorbent article of the present invention.

FIG. 5 is a schematic sectional view along line I-I in FIG. 4.

FIG. 6 is a plan view (expansion plan) of another example of the outer absorbent article of the present invention.

FIG. 7 is a schematic sectional view along line I-I in FIG. 6.

FIG. 8 is a schematic sectional view along line II-II in FIG. 6.

FIG. 9 is a plan view (expansion plan) of one example of an inner absorbent article attached to the outer absorbent article of the present invention.

FIG. 10 is a schematic sectional view along line I-I in FIG. 9.

FIG. 11 is an illustrative diagram for describing attachment of the inner absorbent article to the outer absorbent article of the present invention.

FIG. 12 is an illustrative diagram for describing an engagement state of the inner absorbent article and the outer absorbent article of the present invention.

FIG. 13 is an illustrative diagram showing a general outline of a condensation human test.

DESCRIPTION OF EMBODIMENTS

The outer absorbent article of the present invention comprises an absorbent body composed of at least one absorption layer, wherein the absorbent body includes a water-absorbent resin powder satisfying following requirements of (a) to (d).

(a) Specific surface area measured by BET multipoint method: 0.040 $m^2/g$ to 0.200 $m^2/g$ (b) Vapor blocking rate: 0% to 0.90%

(c) Absorption ratio: 30 g/g to 70 g/g (d) Water retention amount: 20 g/g to 60 g/g First, a water-absorbent resin powder used in the present invention will be described. The water-absorbent resin powder preferably has (a) a specific surface area measured by BET multipoint method in a range from 0.040 $m^2/g$ to 0.200 $m^2/g$. The specific surface area is more preferably 0.042 $m^2/g$ or more, and even more preferably 0.045 $m^2/g$ or more, and is more preferably 0.175 $m^2/g$ or less and even more preferably 0.150 $m^2/g$ or less. When the specific surface area of the water-absorbent resin powder is within the above described range, vapor absorption capability becomes high, and it is possible to prevent vapor from condensing inside the outer absorbent article. It should be noted that measuring of the specific surface area by the BET multipoint method is performed by using krypton gas as adsorption gas.

The water-absorbent resin powder preferably has (b) a vapor blocking ratio of 0% or more, and 0.90% or less. The vapor blocking ratio of the water-absorbent resin is more preferably 0.87% or less, and even more preferably 0.85% or less. If the vapor blocking ratio is too high, the water-absorbent resin powder tends to aggregate after absorbing vapor. As a result, the absorption performance of the absorbent body may deteriorate. It should be noted that, since it is preferable that the blocking due to vapor does not occur, the lower limit value of the vapor blocking ratio is 0%.

The water-absorbent resin powder of the present invention preferably has an absorption ratio in a range from 30 g/g to 70 g/g. The water-absorbent resin powder of the present invention more preferably has an absorption ratio of 32 g/g or more, even more preferably 35 g/g or more, and more preferably has an absorption ratio of 68 g/g or less, even more preferably 65 g/g or less. The absorption ratio is a measure indicating how much water the water-absorbent resin powder can absorb. If the absorption ratio is 30 g/g or more, a large amount of the water-absorbent resin powder does not have to be used in order to maintain an absorption capacity at a predetermined level, and thus it is possible to manufacture a thin absorber. In light of prevention of liquid leakage, the absorption ratio is more preferred if it is greater, but the absorption ratio is more preferably 70 g/g or less. If the absorption ratio is 70 g/g or less, the stability of the water-absorbent resin powder to urine is enhanced.

The water-absorbent resin powder preferably has a water-retaining capacity of 20 g/g or more, more preferably 22 g/g or more, and even more preferably 25 g/g or more, and preferably has a water-retaining capacity of 60 g/g or less, more preferably 57 g/g or less, and even more preferably 55 g/g or less. The water-retaining capacity is a measure indicating how much absorbed liquid the water-absorbent resin powder can retain. If the water-retaining capacity is 20 g/g or more, a large amount of the water-absorbent resin powder does not have to be used in order to maintain a body fluid-retaining capacity at a predetermined level, and thus it is possible to manufacture a thin absorber. In light of prevention of liquid leakage, the water-retaining capacity is more preferred if it is greater, but the water-retaining capacity is more preferably 60 g/g or less. If the water-retaining capacity is 60 g/g or less, the stability of the water-absorbent resin powder to urine is enhanced.

It is possible to adjust the specific surface area, vapor blocking ratio, absorption ratio, and water-retaining capacity of the water-absorbent resin powder by, for example, appropriately selecting the composition of a crosslinked polymer, the type of a surface modifier, the particle size of the water-absorbent resin powder, and the drying condition, etc.

Although there is no particular limitation on the water-absorbent resin powder used in the present invention, as long as it satisfies the requirements of (a) to (d); the water-absorbent resin powder preferably includes (A) a crosslinked polymer mainly composed of acrylic acid and having carboxyl groups thereof being at least partially neutralized. The content of an acrylic acid component forming (A) the crosslinked polymer is preferably 90 mass % or more and more preferably 95 mass % or more, and is preferably 99 mass % or less and more preferably 97 mass % or less. If the content of the acrylic acid component is within the above described range, the obtained water-absorbent resin powder can easily exhibit a desired absorption performance.

Examples of cations for neutralizing at least a part of the carboxyl groups of (A) the crosslinked polymer include, but not particularly limited to, alkali metal ions such as lithium, sodium, and potassium, and alkaline earth metal ions such as magnesium and calcium. Of those described above, at least a part of the carboxyl groups of the crosslinked polymer is preferably neutralized with the sodium ion. It should be noted that, with regard to neutralization of the carboxyl groups of the crosslinked polymer, neutralization may be conducted on the carboxyl groups of the crosslinked polymer which has been obtained by polymerization, or neutralization may be conducted in advance on a monomer which is then used for forming the crosslinked polymer.

The degree of neutralization of the carboxyl groups of the crosslinked polymer is preferably 60 mole % or more, and more preferably 65 mole % or more. This is because there are cases where the absorption performance of the obtained water-absorbent resin powder deteriorates if the degree of neutralization is too low. Furthermore, there is no particular limitation on the upper limit of the degree of neutralization, and all the carboxyl groups may be neutralized. It should be noted that the degree of neutralization is obtained by the following formula.

Degree of neutralization (mole %)=100×[Number of moles of neutralized carboxyl groups in the crosslinked polymer]/[Total number of moles of the carboxyl groups in the crosslinked polymer (including neutralized and unneutralized groups)]

Examples of the crosslinked polymer (A) include those obtained by: crosslinking, using a crosslinking agent (b), particle surfaces of the polymer obtained through polymerization of an unsaturated monomer composition containing a water-soluble ethylenically unsaturated monomer (a1) and/or a hydrolyzable monomer (a2) producing the water-soluble ethylenically unsaturated monomer (a1) by hydrolysis; polymerizing an unsaturated monomer composition containing a water-soluble ethylenically unsaturated monomer (a1) and/or a hydrolyzable monomer (a2) producing the water-soluble ethylenically unsaturated monomer (a1) by hydrolysis and a crosslinking agent (b); crosslinking, using the crosslinking agent (b), particle surfaces of the crosslinked polymer obtained through polymerization of the unsaturated monomer composition containing a water-soluble ethylenically unsaturated monomer (a1) and/or a hydrolyzable monomer (a2) producing the water-soluble ethylenically unsaturated monomer (a1) by hydrolysis, and a crosslinking agent (b).

The water-soluble ethylenically unsaturated monomer (a1) is not particularly limited, but a monomer having at least one water-soluble substituent and an ethylenically unsaturated group, or the like can be used. The water-soluble monomer means a monomer having a property of being dissolved at least in an amount of 100 g in 100 g of water at 25 degrees centigrade. In addition, the hydrolyzable monomer (a2) is hydrolyzed with water at 50 degrees centigrade, by the action of a catalyst (an acid, a base, or the like) where necessary, to produce the water-soluble ethylenically unsaturated monomer (a1). The hydrolysis of the hydrolyzable monomer (a2) may be conducted during or after the polymerization of the crosslinked polymer (A) or both during and after the polymerization of the crosslinked polymer (A). However, the hydrolysis of the hydrolyzable monomer (a2) is preferably conducted after the polymerization of the crosslinked polymer (A) in light of the molecular weight of the obtained water-absorbent resin powder and the like.

Examples of the water-soluble substituent include a carboxyl group, a sulfo group, a sulfoxy group, a phosphono group, a hydroxyl group, a carbamoyl group, an amino group, or salts thereof and an ammonium salt. A salt of a carboxyl group (a carboxylate), a salt of a sulfo group (a sulfonate), and an ammonium salt are preferred. In addition, examples of the salts include salts of alkali metal such as lithium, sodium, and potassium and salts of alkaline earth metal such as magnesium and calcium. The ammonium salt may be any of salts of primary to tertiary amines or a quaternary ammonium salt. Of these salts, in light of absorption properties, alkali metal salts and ammonium salts are preferred, and alkali metal salts are more preferred, and sodium salts are further preferred.

As the water-soluble ethylenically unsaturated monomer having a carboxyl group and/or a salt thereof, an unsaturated carboxylic acid having 3 to 30 carbon atoms and/or a salt thereof are preferred. Specific examples of the water-soluble ethylenically unsaturated monomer having a carboxyl group and/or a salt thereof include unsaturated monocarboxylic acids and/or salts thereof such as (meth)acrylic acid, (meth) acrylic acid salt, crotonic acid, and cinnamic acid; unsaturated dicarboxylic acids and/or salts thereof such as maleic acid, maleate, fumaric acid, citraconic acid, and itaconic acid; and monoalkyl (1 to 8 carbon atoms) esters of unsaturated dicarboxylic acids and/or salts thereof such as maleic acid monobutyl ester, fumaric acid monobutyl ester, ethylcarbitol monoester of maleic acid, ethylcarbitol monoester of fumaric acid, citraconic acid monobutyl ester, and itaconic acid glycol monoester. It is noted that in the description of the present invention, "(meth)acrylic" means "acrylic" and/or "methacrylic".

As a water-soluble ethylenically unsaturated monomer having a sulfo group and/or a salt thereof, a sulfonic acid having 2 to 30 carbon atoms and/or a slat thereof are preferred. Specific examples of the water-soluble ethylenically unsaturated monomer having a sulfo group and/or a salt thereof include aliphatic or aromatic vinyl sulfonic acids such as vinyl sulfonic acid, (meth)allyl sulfonic acid, styrene sulfonic acid, and alpha-methyl styrene sulfonic acid; (meth) acryloyl-containing alkyl sulfonic acids such as (meth) acryloxy propyl sulfonic acid, 2-hydroxy-3-(meth)acryloxy propyl sulfonic acid, 2-(meth)acryloylamino-2,2-dimethyl-ethane sulfonic acid, 3-(meth)acryloxyethane sulfonic acid, 2-(meth)acrylamide-2-methylpropane sulfonic acid, and 3-(meth)acrylamide-2-hydroxypropane sulfonic acid; and alkyl(meth)allyl sulfosuccinate.

Examples of a water-soluble ethylenically unsaturated monomer having a sulfoxy group and/or a salt thereof include sulfate ester of hydroxyalkyl (meth)acrylate; and sulfate ester of polyoxyalkylene mono(meth)acrylate.

Examples of a water-soluble ethylenically unsaturated monomer having a phosphono group and/or a salt thereof include phosphate monoesters of (meth)acrylic acid hydroxyalkyl, phosphate diesters of (meth)acrylic acid hydroxyalkyl, and (meth)acrylic acid alkylphosphonic acids.

Examples of a water-soluble ethylenically unsaturated monomer having a hydroxyl group include mono-ethylenically unsaturated alcohols having 3 to 15 carbon atoms such as (meth)allyl alcohol and (meth)propenyl alcohol; mono-ethylenically unsaturated carboxylates or mono-ethylenically unsaturated ethers of bivalent to hexavalent polyols such as alkylene glycol having 2 to 20 carbon atoms, glycerin, sorbitan, diglycerin, pentaerythritol, and polyalkylene (2 to 4 carbon atoms) glycol (weight average molecular weight: 100 to 2000). Specific examples of them include hydroxyethyl(meth)acrylate, hydroxypropyl(meth)acrylate, tri-ethyleneglycol(meth)acrylate, and poly-oxyethylene-oxypropylene mono(meth)allyl ether.

Examples of a water-soluble ethylenically unsaturated monomer having a carbamoyl group include (meth)acrylamide; N-alkyl (1 to 8 carbon atoms) (meth)acrylamides such as N-methyl acrylamide; N,N-dialkyl (alkyl having 1 to 8 carbon atoms) acrylamides such as N,N-dimethyl acrylamide and N,N-di-n- or i-propyl acrylamide; N-hydroxyalkyl (1 to 8 carbon atoms) (meth)acrylamides such as N-methylol (meth)acrylamide and N-hydroxyethyl (meth) acrylamide; and N,N-dihydroxyalkyl (1 to 8 carbon atoms) (meth)acrylamides such as N,N-dihydroxyethyl (meth)acrylamide. As an unsaturated monomer having a group composed of an amide, in addition to them, vinyl lactams having 5 to 10 carbon atoms (N-vinyl pyrrolidone, etc.) and the like can also be used.

Examples of a water-soluble ethylenically unsaturated monomer having an amino group include an amino group-containing ester of a mono-ethylenically unsaturated mono- or di-carboxylic acid and an amino group-containing amide of a mono-ethylenically unsaturated mono- or di-carboxylic acid. As the amino group-containing ester of a mono-ethylenically unsaturated mono- or di-carboxylic acid, dialky-laminoalkyl(meth)acrylate, di(hydroxyalkyl)amino-alkyl ester, morpholinoalkyl ester, and the like can be used, and examples thereof include dimethylaminoethyl (meth) acrylate, diethylamino (meth)acrylate, morpholinoethyl (meth)acrylate, dimethylaminoethyl fumarate, and dimethylaminoethyl malate. As the amino group-containing amide of a mono-ethylenically unsaturated mono- or di-carboxylic acid, monoalkyl (meth)acrylamide is preferred, and examples thereof include dimethyl-laminoethyl (meth)acrylamide and diethylaminoethyl (meth)acrylamide. As the water-soluble ethylenically unsaturated monomer having an amino group, in addition to them, vinylpyridines such as 4-vinylpyridine and 2-vinylpyridine can also be used.

The hydrolyzable monomer (a2) producing the water-soluble ethylenically unsaturated monomer (a1) by hydrolysis is not particularly limited, but an ethylenically unsaturated monomer having at least one hydrolyzable substituent that becomes a water-soluble substituent by hydrolysis is preferred. Examples of the hydrolyzable substituent include a group containing an acid anhydride, a group containing an ester linkage, and a cyano group.

As an ethylenically unsaturated monomer having a group containing an acid anhydride, an unsaturated dicarboxylic anhydride having 4 to 20 carbon atoms is used, and examples thereof include maleic anhydride, itaconic anhydride, and citraconic anhydride. Examples of an ethylenically unsaturated monomer having a group containing an ester linkage include lower alkyl esters of mono-ethylenically unsaturated carboxylic acids such as methyl (meth) acrylate and ethyl (meth)acrylate; and esters of mono-ethylenically unsaturated alcohols such as vinyl acetate and (meth)allyl acetate. Examples of an ethylenically unsaturated monomer having a cyano group include vinyl group-containing nitrile compounds having 3 to 6 carbon atoms such as (meth)acrylonitrile and 5-hexenenitrile.

As the water-soluble ethylenically unsaturated monomer (a1) and the hydrolyzable monomer (a2), those described in Japanese Patent No. 3648553, Japanese Patent Publication No. 2003-165883, Japanese Patent Publication No. 2005-75982, and Japanese Patent Publication No. 2005-95759 can be further used. As each of the water-soluble ethylenically unsaturated monomer (a1) and the hydrolyzable monomer (a2), a single monomer or a mixture of two or more monomers may be used.

In addition to the water-soluble ethylenically unsaturated monomer (a1) and the hydrolyzable monomer (a2), another vinyl monomer (a3) that is copolymerizable with these monomers can be used for the unsaturated monomer composition. As the copolymerizable other vinyl monomer (a3), hydrophobic vinyl monomers and the like can be used, but it is not limited to them. As the other vinyl monomer (a3), the following vinyl monomers (i) to (iii) and the like are used.

(i) Aromatic ethylenically unsaturated monomers having 8 to 30 carbon atoms;
Styrenes such as styrene, alpha-methylstyrene, vinyltoluene, and hydroxystyrene; vinylnaphthalene; and halogen substitutions of styrene such as dichlorostyrene.

(ii) Aliphatic ethylenically unsaturated monomers having 2 to 20 carbon atoms;
Alkenes such as ethylene, propylene, butene, isobutylene, pentene, heptene, di-isobutylene, octene, dodecene, and octadecene; and alkadienes such as butadiene, and isoprene.

(iii) Alicyclic ethylenically unsaturated monomers having 5 to 15 carbon atoms;
Mono-ethylenically unsaturated monomers such as pinene, limonene, and indene; and polyethylenic vinyl-polymerizable monomers such as cyclopentadiene, bicyclopentadiene, and ethylidene norbornene.

As the other vinyl monomer (a3), those described in Japanese Patent No. 3648553, Japanese Publication No. 2003-165883, Japanese Patent Publication No. 2005-75982, and Japanese Patent Publication No. 2005-95759 can be further used.

From the aspect of providing the crosslinked polymer mainly composed of acrylic acid, as the water-soluble ethylenically unsaturated monomer (a1) and/or the hydrolyzable monomer (a2) producing the water-soluble ethylenically unsaturated monomer (a1) by hydrolysis, acrylic acid or a salt of acrylic acid (a1), or a hydrolyzable monomer (a2) producing acrylic acid or the salt of acrylic acid is preferable. The content of acrylic acid or the salt of acrylic acid (a1), or the hydrolyzable monomer (a2) producing acrylic acid or the salt of acrylic acid in the unsaturated monomer composition constituting the crosslinked polymer is preferably 90 mass % or more, more preferably 95 mass % or more, and is preferably 99 mass % or less, more preferably 97 mass % or less.

Examples of the crosslinking agent (b) can include a crosslinking agent (b1) having two or more ethylenically unsaturated groups; a crosslinking agent (b2) having at least one functional group that can react with a water-soluble substituent of the water-soluble ethylenically unsaturated monomer (a1) and/or a water-soluble substituent produced by hydrolysis of the hydrolyzable monomer (a2) and at least one ethylenically unsaturated group; and a crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2).

Examples of the crosslinking agent (b1) having two or more ethylenically unsaturated groups include bis(meth) acrylamides having 8 to 12 carbon atoms, poly(meth)acrylates of polyols having 2 to 10 carbon atoms, polyallylamines having 2 to 10 carbon atoms, and poly(meth)allyl ethers of polyols having 2 to 10 carbon atoms. Specific examples of them include N,N'-methylene bis(meth)acrylamide, ethylene glycol di(meth)acrylate, poly (polymerization degree of 2 to 5) ethylene glycol di(meth)acrylate, propylene glycol di(meth)acrylate, glycerol (di or tri)acrylate, trimethylol propane triacrylate, diallylamine, triallylamine, triallylcyanurate, triallylisocyanurate, tetraallyloxyethane, pentaerythritol diallyl ether, pentaerythritol triallyl ether, pentaerythritol tetraallyl ether, and diglycerin di(meth)acrylate.

Examples of the crosslinking agent (b2) having at least one functional group that can react with a water-soluble substituent of the water-soluble ethylenically unsaturated monomer (a1) and/or a water-soluble substituent produced by hydrolysis of the hydrolyzable monomer (a2) and at least one ethylenically unsaturated group include ethylenically unsaturated compounds having 6 to 8 carbon atoms and an epoxy group, ethylenically unsaturated compounds having 4 to 8 carbon atoms and a hydroxyl group, and ethylenically unsaturated compounds having 4 to 8 carbon atoms and an isocyanato group. Specific examples of them include glycidyl (meth)acrylate, N-methylol (meth)acrylamide, hydroxyethyl (meth)acrylate, and isocyanato ethyl (meth) acrylate.

Examples of the crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2) can include polyhydric alcohols, polyvalent glycidyls, polyvalent amines, polyvalent aziridines, and polyvalent isocyanates. Examples of polyvalent glycidyl compounds include ethylene glycol diglycidyl ether and glycerin diglycidyl ether. Examples of polyvalent amine compounds include ethylenediamine, diethylenetriamine, triethylenetetramine, tetraethylenepentamine, pentaethylene-hexamine, and polyethyleneimine. Examples of polyvalent aziridine compounds include Chemitite PZ-33 {2,2-bishydroxymethylbutanol-tris (3-(1-aziridinyl)propionate)}, Chemitite HZ-22 {1,6-hexamethylenediethyleneurea}, and Chemitite DZ-22 {diphenylmethane-bis-4,4'-N,Ni'-diethyleneurea}, available from Nippon Shokubai Co., Ltd. Examples of polyvalent polyisocyanate compounds include 2,4-tolylene diisocyanate and hexamethylene diisocyanate. These crosslinking agents may be used singly or two or more of them may be used in combination.

When using the crosslinking agent (b) in polymerization, in light of absorbing performance (in particular, an absorption amount, an absorption speed, etc.), as the (internal) crosslinking agent, the crosslinking agent (b1) having two or more ethylenically unsaturated groups is preferred, poly(meth)allyl ethers of polyols having 2 to 10 carbon atoms are more preferred, triallylcyanurate, triallylisocyanurate, tetraallyloxyethane, or pentaerythritol triallyl ether is further preferred, and pentaerythritol triallyl ether is most preferred.

When using (b) the crosslinking agent for crosslinking the surface of the polymer particle, from a standpoint of absorption performance etc., of the water-absorbent resin powder, the crosslinking agent (surface crosslinking agent) preferably includes the crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2), more preferably polyvalent glycidyl, even more preferably ethylene glycol diglycidyl ether and glycerin diglycidyl ether, and most preferably ethylene glycol diglycidyl ether.

As the crosslinking agent (b), those described in Japanese Patent No. 3648553, Japanese Patent Publication No. 2003-165883, Japanese Patent Publication No. 2005-75982, and Japanese Patent Publication No. 2005-95759 can be further used.

When conducting the surface crosslinking, the amount of (b) the crosslinking agent to be added is preferably 0.001 part by mass or more, more preferably 0.002 part by mass or more, and even more preferably 0.003 part by mass or more, and is preferably 7 parts by mass or less, more preferably 5 parts by mass or less, and even more preferably 4 parts by mass or less, with respect to 100 parts by mass of the resin fine particles before surface crosslinking. If the amount of the crosslinking agent (b) to be added is within the above described range, the absorption performance becomes better.

As the method for polymerizing the crosslinked polymer (A), a conventionally known method and the like can be used, and a solution polymerization method, an emulsion polymerization method, a suspension polymerization method, and a reversed-phase suspension polymerization method can be used. In addition, a polymerization liquid at the polymerization may be in the form of a thin film, mist, or the like. As the method for controlling the polymerization, an adiabatic polymerization method, a temperature-controlled polymerization method, an isothermal polymerization method, and the like can be used. As the polymerization method, the solution polymerization method and the reversed-phase suspension polymerization method is preferable in view of the processability, and the reversed-phase suspension polymerization method is more preferable in view of adjusting the BET specific surface area. In the following, although a reversed phase suspension polymerization method is described as the mode of the method for producing the crosslinked polymer (A) used in the present invention, the crosslinked polymer (A) used in the present invention is not limited to those obtained by a reversed phase suspension polymerization method.

The reversed-phase suspension polymerization method is a method of dispersing, suspending, and polymerizing a water-soluble polymerizable monomer in a hydrophobic organic solvent under the presence of a dispersant. In the present invention, a dispersant used for the reversed-phase suspension polymerization method preferably contains a phosphate (salt) (D) of an aliphatic alcohol alkylene oxide adduct (C). By using the dispersant containing the phosphate (salt) (D) of the aliphatic alcohol alkylene oxide adduct (C), it becomes easy to obtain a crosslinked polymer having a small particle size and a large BET specific surface area. Examples of the phosphate (salt) (D) of the aliphatic alcohol alkylene oxide adduct (C) include phosphoric acid monoester (salt), phosphoric acid diester (salt), and an ester (salt) of polyphosphoric acid. The phosphate (salt) (D) preferably includes at least one type of phosphate (salt) represented by general formula (1). The dispersant containing the phosphate (salt) represented by the general formula (1) has excellent dispersion stability. It should be noted that the phosphate (D) contained in the dispersant preferably includes an alkylene oxide adduct phosphoric acid ester represented by general formula (1), and more preferably consists of the phosphate represented by general formula (1).

Chem 1

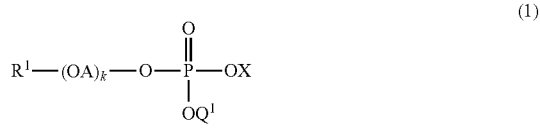

(1)

In general formula (1), $R^1$ represents an acyclic aliphatic hydrocarbon group having a carbon number of 8 to 24 or a cyclic aliphatic hydrocarbon group having a carbon number of 8 to 24, OA represents at least one kind of oxyalkylene group having a carbon number of 2 to 4, k represents an integer of 1 to 20, and X indicates a group represented by $Q^2$ or $R^2$—$(OA')_{k'}$—. $Q^1$ and $Q^2$ represent hydrogen atom, an alkali metal, or a quarternary ammonium. $R^2$ represents an aliphatic hydrocarbon group having a carbon number of 1 to 24, OA' represents at least one kind of oxyalkylene group having a carbon number of 2 to 4, and k' represents an integer of 1 to 20.

Examples of the alkali metal include sodium, potassium, lithium, and the like; and the alkali metal is preferably sodium. Examples of the quarternary ammonium include tetramethyl ammonium, tetraethyl ammonium, trimethyl ethyl ammonium, trimethyl benzyl ammonium, and the like; and the quarternary ammonium is preferably tetramethyl ammonium and tetraethyl ammonium.

Furthermore, $R^2$ represents a group similar to $R^1$ and an acyclic aliphatic hydrocarbon group having a carbon number of 1 to 7; and a preferable range thereof is identical to that of $R^1$, and may be identical to or different from $R^1$. As the acyclic aliphatic hydrocarbon group having a carbon number of 1 to 7, an alkyl group having a carbon number of 1 to 7, an alkenyl group having a carbon number of 3 to 7, or the like is used. Examples of the alkyl group include methyl group, ethyl group, propyl group, isopropyl group, butyl group, hexyl group, heptyl group, and the like. Examples of the alkenyl group include propenyl group, butenyl group, hexenyl group, heptenyl group, and the like. Furthermore, OA' represents a group similar to OA, and a preferable range thereof is also the same. In addition, OA' may be identical to or different from OA; however, OA' is preferably identical to OA. Furthermore, k' represents an integer of 1 to 20, wherein a range of k' is preferably identical to k, and k' may be identical to or different from k. In addition, the group represented by $R^2-(OA')_{k'}$- is preferably identical to a group represented by $R^1-(OA)_{k}$-.

The phosphate (salt) (D) more preferably includes at least one kind of phosphate (salt) represented by the general formula (2). By including the phosphate (salt) represented by the general formula (2), the dispersant for reversed-phase suspension polymerization can have more excellent dispersion stability. It should be noted that the phosphate (D) contained in the dispersant more preferably includes an alkylene oxide adduct phosphoric acid ester represented by the general formula (2), and more preferably consists of a phosphate represented by the general formula (2).

Chem 2

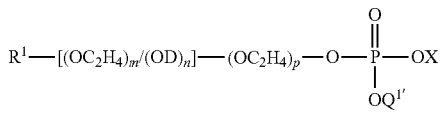

In general formula (2), $R^1$ represents an aliphatic hydrocarbon group having a carbon number of 8 to 24, and OD represents an oxyalkylene group having a carbon number of 3 or 4. m represents 0 or an integer of 1 to 20, n represents 0 or an integer of 1 to 20, p represents 0 or an integer of 1 to 20, (m+n+p) is an integer of 1 to 20, and (m+p)/(m+n+p) is 0.5 to 1. When m is not equal to 0 and n is not equal to 0, $\{(OC_2H_4)_m/(OD)_n\}$ indicates block addition and/or random addition. Furthermore, X indicates a group represented by $Q^{2'}$ or $R^2-[(OC_2H_4)_{m'}/(OD')_{n'}]-(OC_2H_4)_{p'}-$. $Q^{1'}$ and $Q^{2'}$ represent hydrogen atom, an alkali metal, or a quarternary ammonium. $R^2$ represents an aliphatic hydrocarbon group having a carbon number of 1 to 24, and OD' represents an oxyalkylene group having a carbon number of 3 or 4. m' represents 0 or an integer of 1 to 20, n' represents 0 or an integer of 1 to 20, p' represents 0 or an integer of 1 to 20, (m'+n'+p') is an integer of 1 to 20, and (m'+p')/(m'+n'+p') is 0.5 to 1. When m is not equal to 0 and n is not equal to 0, $\{(OC_2H_4)_{m'}/(OD')_{n'}\}$ indicates block addition and/or random addition.

OD', m', n', p', (m'+n'+p'), and (m'+p')/(m'+n'+p'), are identical to OD, m, n, p, (m+n+p), and (m+p)/(m+n+p), respectively; and their preferable ranges are also the same. It should be noted that OD' may be identical to or different from OD; however, OD' is preferably identical to OD. Furthermore, m', n', p', (m'+n'+p'), and (m'+p')/(m'+n'+p'), may be identical to or different from OD, m, n, p, (m+n+p), and (m+p)/(rn+n+p), respectively. When m' is not equal to 0 and n' is not equal to 0, $\{(OC_2H_4)_{m'}/(OD')_{n'}\}$ indicates block addition and/or random addition. Furthermore, a group represented by $R^2-[(OC_2H_4)_{m'}/(OD')_{n'}]-(OC_2H_4)_{p'}-$ is preferably identical to a group represented by $R^1-[(OC_2H_4)_{m'}/(OD)_n]-(OC_2H_4)_p-$.

When X is $Q^2$ or $Q^{2'}$ in general formula (1) or (2), the phosphate (salt) (D) represented by these formulae is a phosphoric acid monoester (salt); and when X is a group represented by $R^2-(OA')_{k'}-$ or a group represented by $R^2-[(OC_2H_4)_{m'}/(OD')_{n'}]-(OC_2H_4)_{p'}-$, the phosphate (salt) (D) is a phosphoric acid diester (salt). With regard to the phosphoric acid monoester (salt) and phosphoric acid diester (salt), depending on the particle size or bulk density of suspended particles (polymer), they may be used alone or may be used as a mixture of the monoester (salt) and the diester (salt). More specifically, the phosphoric acid monoester (salt) is preferably used for increasing the bulk density of the suspended particles (polymer), and the phosphoric diester (salt) is preferably used for decreasing the particle size of the suspended particles (polymer). Furthermore, in order to obtain suspended particles (polymer) having a small particle size and a large bulk density, a mixture of the monoester (salt) and the diester (salt) is preferably used. In this case, the ratio (mole ratio) of the phosphoric acid monoester (salt)/phosphoric acid diester (salt) is preferably 1.0 to 2.0, more preferably 1.1 to 1.9, even more preferably 1.2 to 1.8, and most preferably 1.25 to 1.75. Thus, the upper limit of the ratio (mole ratio) is preferably 2.0, more preferably 1.9, even more preferably 1.8, and most preferably 1.75; and the lower limit is preferably 1.0, more preferably 1.1, even more preferably 1.2 and most preferably 1.25.

Preferable examples of the phosphate (salt) represented by the general formula (1) or (2) include the following (I) to (III).

(I) Phosphoric Acid Monoester (Salt) of Aliphatic Alcohol Alkylene Oxide Adduct (C)

(I-1) Aliphatic Hydrocarbon Polyoxyethylene Phosphoric Acid Monoester (Salt)

octyl pentaoxyethylene phosphoric acid monoester (sodium salt), dodecyl hexaoxyethylene phosphoric acid monoester (potassium salt), tridecyl heptaoxyethylene phosphoric acid monoester (sodium salt), stearyl octaoxyethylene phosphoric acid monoester (sodium salt), eicosenyl pentaoxyethylene phosphoric acid monoester (sodium salt), eicosenyl decaoxyethylene phosphoric acid monoester (sodium salt), docosenyl pentaoxyethylene phosphoric acid monoester (sodium salt), docosenyl decaoxyethylene phosphoric acid monoester (sodium salt), ethylcyclohexyl pentaoxyethylene phosphoric acid monoester (potassium salt), propylcyclohexyl hexaoxyethylene phosphoric acid monoester (sodium salt), octylcyclohexyl heptaoxyethylene phosphoric acid monoester (tetramethyl ammonium salt), nonylcyclohexyl heptaoxyethylene phosphoric acid monoester (sodium salt), stearylcyclohexyl nonaoxyethylene phosphoric acid monoester (sodium salt), etc.

(I-2) Aliphatic Hydrocarbon Polyoxypropylene Phosphoric Acid Monoester (Salt)

Octyl tetraoxypropylene phosphoric acid monoester (sodium salt), dodecyl pentaoxypropylene phosphoric acid monoester (potassium salt), tridecyl hexaoxypropylene phosphoric acid monoester (sodium salt), stearyl heptaoxypropylene phosphoric acid monoester (sodium salt), eicosenyl pentaoxypropylene phosphoric acid monoester (sodium salt), eicosenyl decaoxypropylene phosphoric acid monoester (sodium salt), docosenyl pentaoxypropylene phosphoric acid monoester (sodium salt), docosenyl decaoxypropylene phosphoric acid monoester (sodium salt), ethylcyclohexyl trioxypropylene phosphoric acid monoester (sodium salt), propylcyclohexyl pentaoxypropylene phosphoric acid monoester (sodium salt), octylcyclohexyl pentaoxypropylene phosphoric acid monoester (sodium salt), nonylcyclohexyl hexaoxypropylene phosphoric acid monoester (sodium salt), stearylcyclohexyl α-taoxypropylene phosphoric acid monoester (sodium salt), etc.

(I-3) Aliphatic Hydrocarbon Polyoxybutylene Phosphoric Acid Monoester (Salt)

Octyl trioxybutylene phosphoric acid monoester (sodium salt), dodecyl tetraoxybutylene phosphoric acid monoester (sodium salt), tridecyl tetraoxybutylene phosphoric acid monoester (sodium salt), stearyl hexaoxybutylene phosphoric acid monoester (potassium salt), eicosenyl pentaoxybutylene phosphoric acid monoester (sodium salt), eicosenyl decaoxybutylene phosphoric acid monoester (sodium salt), docosenyl pentaoxybutylene phosphoric acid monoester (sodium salt), docosenyl decaoxybutylene phosphoric acid monoester (sodium salt), ethylcyclohexyl dioxybutylene phosphoric acid monoester (sodium salt), propylcyclohexyl tetraoxybutylene phosphoric acid monoester (sodium salt), octylcyclohexyl tetraoxybutylene phosphoric acid monoester (potassium salt), nonylcyclohexyl pentaoxybutylene phosphoric acid monoester (sodium salt), stearylcyclohexyl heptaoxybutylene phosphoric acid monoester (sodium salt), etc.

(I-4) Aliphatic Hydrocarbon Polyoxyethylene-Polyoxypropylene Phosphoric Acid Monoester (Salt)

Octyl tetraoxyethylene-monooxypropylene phosphoric acid monoester (sodium salt), octyl dioxyethylene-monooxypropylene-dioxyethylene phosphoric acid monoester (sodium salt), dodecyl pentaoxyethylene-monooxypropylene phosphoric acid monoester (sodium salt), dodecyl dioxyethylene-monooxypropylene-trioxyethylene phosphoric acid monoester (sodium salt), tridecyl hexaoxyethylene-monooxypropylene phosphoric acid monoester (potassium salt), tridecyl dioxyethylene-monooxypropylene-tetraoxyethylene phosphoric acid monoester (sodium salt), stearyl hexaoxyethylene-dioxypropylene phosphoric acid monoester (sodium salt), stearyl dioxyethylene-dioxypropylene-tetraoxyethylene phosphoric acid monoester (sodium salt), eicosenyl tetraoxyethylene-monooxypropylene phosphoric acid monoester (sodium salt), eicosenyl dioxyethylene-monooxypropylene-dioxyethylene phosphoric acid monoester (sodium salt), eicosenyl nonaoxyethylene-monooxypropylene phosphoric acid monoester (sodium salt), eicosenyl dioxyethylene-monooxypropylene-heptaoxyethylene phosphoric acid monoester (sodium salt), docosenyl tetraoxyethylene-monooxypropylene phosphoric acid monoester (sodium salt), docosenyl dioxyethylene-monooxypropylene-dioxyethylene phosphoric acid monoester (sodium salt), docosenyl nonaoxyethylene-monooxypropylene phosphoric acid monoester (sodium salt), docosenyl dioxyethylene-monooxypropylene-heptaoxyethylene phosphoric acid monoester (sodium salt), ethylcyclohexyl tetraoxyethylene-monooxypropylene phosphoric acid monoester (sodium salt), propylcyclohexyl tetraoxyethylene-monooxypropylene phosphoric acid monoester (potassium salt), octylcyclohexyl hexaoxyethylene-monooxypropylene phosphoric acid monoester (sodium salt), nonylcyclohexyl hexaoxyethylene-dioxypropylene phosphoric acid monoester (sodium salt), stearylcyclohexyl hexaoxyethylene-dioxypropylene phosphoric acid monoester (sodium salt), etc.

(II) Phosphoric Acid Diester (Salt) of Aliphatic Alcohol Alkylene Oxide Adduct (C)

(II-1) Aliphatic Alcohol Polyoxyethylene Phosphoric Acid Diester (Salt)

Bis(octyl pentaoxyethylene) phosphoric acid diester (sodium salt), bis(dodecyl hexaoxyethylene) phosphoric acid diester (potassium salt), bis(tridecyl heptaoxyethylene) phosphoric acid diester (sodium salt), bis(stearyl octaoxyethylene) phosphoric acid diester (sodium salt), bis(eicosenyl pentaoxyethylene) phosphoric acid diester (sodium salt), bis(eicosenyl decaoxyethylene) phosphoric acid diester (sodium salt), bis(docosenyl pentaoxyethylene) phosphoric acid diester (sodium salt), bis(docosenyl decaoxyethylene) phosphoric acid diester (sodium salt), bis(ethylcyclohexyl pentaoxyethylene) phosphoric acid diester (potassium salt), bis(propyl cyclohexyl hexaoxyethylene) phosphoric acid diester (sodium salt), bis(octylcyclohexyl heptaoxyethylene) phosphoric acid diester (tetramethyl ammonium salt), bis (nonylcyclohexyl heptaoxyethylene) phosphoric acid diester (sodium salt), bis(stearylcyclohexyl nonaoxyethylene) phosphoric acid diester (sodium salt), etc.

(II-2) Aliphatic Alcohol Polyoxypropylene Phosphoric Acid Diester (Salt)

Bis(octyl tetraoxypropylene) phosphoric acid diester (sodium salt), bis(dodecyl pentaoxypropylene) phosphoric acid diester (potassium salt), bis(tridecyl hexaoxypropylene) phosphoric acid diester (sodium salt), bis(stearyl heptaoxypropylene) phosphoric acid diester (sodium salt), bis(eicosenyl pentaoxypropylene) phosphoric acid diester (sodium salt), bis(eicosenyl de-caoxypropylene) phosphoric acid diester (sodium salt), bis(docosenyl pentaoxypropylene) phosphoric acid diester (sodium salt), bis(docosenyl decaoxypropylene) phosphoric acid diester (sodium salt), bis (ethylcyclohexyl trioxypropylene) phosphoric acid diester (sodium salt), bis(propylcyclohexyl pentaoxypropylene) phosphoric acid diester (sodium salt), bis(octylcyclohexyl pentaoxypropylene) phosphoric acid diester (sodium salt), bis(nonylcyclohexyl hexaoxypropylene) phosphoric acid diester (sodium salt), bis(stearylcyclohexyl octaoxypropylene) phosphoric acid diester (sodium salt), etc.

(II-3) Aliphatic Alcohol Polyoxybutylene Phosphoric Acid Diester (Salt)

Bis(octyl trioxybutylene) phosphoric acid diester (sodium salt), bis(dodecyl tetraoxybutylene) phosphoric acid diester (sodium salt), bis(tridecyl tetraoxybutylene) phosphoric acid diester (sodium salt), bis(stearyl hexaoxybutylene) phosphoric acid diester (sodium salt), bis(eicosenyl pentaoxybutylene) phosphoric acid diester (sodium salt), bis(eicosenyl decaoxybutylene) phosphoric acid diester (sodium salt), bis(docosenyl pentaoxybutylene) phosphoric acid diester (sodium salt), bis(docosenyl decaoxybutylene) phosphoric acid diester (sodium salt), bis(ethylcyclohexyl dioxybutylene) phosphoric acid diester (sodium salt), bis(propylcyclohexyl tetraoxybutylene) phosphoric acid diester (potassium salt), bis(octylcyclohexyl tetraoxybutylene) phosphoric acid diester (sodium salt), bis(nonylcyclohexyl pentaoxybutylene) phosphoric acid diester (sodium salt), bis(stearylcyclohexyl heptaoxybutylene) phosphoric acid diester (sodium salt), etc.

(II-4) Aliphatic Alcohol Polyoxyethylene-Polyoxypropylene Phosphoric Acid Diester (salt)

Bis(octyl tetraoxyethylene-monooxypropylene) phosphoric acid diester (sodium salt), bis(octyl dioxyethylene-monooxypropylene-dioxyethylene) phosphoric acid diester (sodium salt), bis(dodecyl pentaoxyethylene-monooxypropylene) phosphoric acid diester (sodium salt), bis(dodecyl dioxyethylene-monooxypropylene-trioxyethylene) phosphoric acid diester (sodium salt), bis(tridecyl hexaoxyethylene-monooxypropylene) phosphoric acid diester (sodium salt), bis(tridecyl dioxyethylene-monooxypropylene-tetraoxyethylene) phosphoric acid diester (potassium salt), bis(stearyl hexaoxyethylene-dioxypropylene) phosphoric acid diester (sodium salt), bis(stearyl dioxyethylene-dioxypropylene-tetraoxyethylene) phosphoric acid diester (sodium salt), bis(eicosenyl tetraoxyethylene-monooxypropylene) phosphoric acid diester (sodium salt), bis(eicosenyl dioxyethylene-monooxypropylene-dioxyethylene) phosphoric acid diester (sodium salt), bis(eicosenyl nonaoxyethylene-monooxypropylene) phosphoric acid diester (sodium salt), bis(eicosenyl dioxyethylene-monooxypropylene-heptaoxyethylene) phosphoric acid diester (sodium salt), bis(docosenyl tetraoxyethylene-monooxypropylene) phosphoric acid diester (sodium salt), bis(docosenyl dioxyethylene-monooxypropylene-dioxyethylene) phosphoric acid diester (sodium salt), bis(docosenyl nonaoxyethylene-monooxypropylene) phosphoric acid diester (sodium salt), bis(docosenyl dioxyethylene-monooxypropylene-heptaoxyethylene) phosphoric acid diester (sodium salt), bis(ethylcyclohexyl tetraoxyethylene-monooxypropylene) phosphoric acid diester (sodium salt), bis(propylcyclohexyl tetraoxyethylene-monooxypropylene) phosphoric acid diester (sodium salt), bis(octylcyclohexyl hexaoxyethylene-monooxypropylene) phosphoric acid diester (sodium salt), bis(nonylcyclohexyl hexaoxyethylene-dioxypropylene) phosphoric acid diester (sodium salt), bis (stearylcyclohexyl hexaoxyethylene-dioxypropylene) phosphoric acid diester (sodium salt), etc.

(III) Phosphoric acid diester (salt) in which a group represented by $R^1$—$(OA)_k$- or $R^1$—$[(OC_2H_4)_m/(OD)_n]$—$(OC_2H_4)_p$— is different from a group represented by $R^2$—$(OA')_{k'}$- or $R^2$—$[(OC_2H_4)_{m'}/(OD')_{n'}]$—$(OC_2H_4)_{p'}$—.

(III-1) Aliphatic Alcohol Polyoxyethylene Phosphoric Acid Diester (Salt)

Octyl pentaoxyethylene-methyl trioxyethylene phosphoric acid diester (sodium salt), dodecyl hexaoxyethylene-methyl trioxyethylene phosphoric acid diester (potassium salt), tridecyl heptaoxyethylene-methyl trioxyethylene phosphoric acid diester (sodium salt), stearyl octaoxyethylene-methyl trioxyethylene phosphoric acid diester (sodium salt), eicosenyl pentaoxyethylene-methyl trioxyethylene phosphoric acid diester (sodium salt), eicosenyl decaoxyethylene-methyl trioxyethylene phosphoric acid diester (sodium salt), docosenyl pentaoxyethylene-methyl trioxyethylene phosphoric acid diester (sodium salt), docosenyl decaoxyethylene-methyl trioxyethylene phosphoric acid diester (sodium salt), ethylcyclohexyl pentaoxyethylene-methyl trioxyethylene phosphoric acid diester (potassium salt), propylcyclohexyl hexaoxyethylene-methyl trioxyethylene phosphoric acid diester (sodium salt), octylcyclohexyl heptaoxyethylene-methyl trioxyethylene phosphoric acid diester (tetramethyl ammonium salt), nonylcyclohexyl heptaoxyethylene-methyl trioxyethylene phosphoric acid diester (sodium salt), stearylcyclohexyl nonaoxyethylene-methyl trioxyethylene phosphoric acid diester (sodium salt), etc.

(III-2) Aliphatic Alcohol Polyoxypropylene-Aliphatic Alcohol Polyoxyethylene Phosphoric Acid Diester (Salt)

Octyl tetraoxypropylene-methyl trioxyethylene phosphoric acid diester (sodium salt), dodecyl pentaoxypropylene-methyl trioxyethylene phosphoric acid diester (potassium salt), tridecyl hexaoxypropylene-methyl trioxyethylene phosphoric acid diester (sodium salt), stearyl heptaoxypropylene-methyl trioxyethylene phosphoric acid diester (sodium salt), eicosenyl pentaoxypropylene-methyl trioxyethylene phosphoric acid diester (sodium salt), eicosenyl decaoxypropylene-methyl trioxyethylene phosphoric acid diester (sodium salt), docosenyl pentaoxypropylene-methyl trioxyethylene phosphoric acid diester (sodium salt), docosenyl de-caoxypropylene-methyl trioxyethylene phosphoric acid diester (sodium salt), ethylcyclohexyl trioxypropylene-methyl trioxyethylene phosphoric acid diester (sodium salt), propylcyclohexyl pentaoxypropylene-methyl trioxyethylene phosphoric acid diester (sodium salt), octylcyclohexyl penta-oxypropylene-methyl trioxyethylene phosphoric acid diester (sodium salt), nonylcyclohexyl hexaoxypropylene-methyl trioxyethylene phosphoric acid diester (sodium salt), stearylcyclohexyl octaoxypropylene-methyl trioxyethylene phosphoric acid diester (sodium salt), etc.

(III-3) Aliphatic Alcohol Polyoxybutylene-Aliphatic Alcohol Polyoxyethylene Phosphoric Acid Diester (Salt)

Octyl trioxybutylene-methyl trioxyethylene phosphoric acid diester (sodium salt), dodecyl tetraoxybutylene-methyl trioxyethylene phosphoric acid diester (sodium salt), tridecyl tetraoxybutylene-methyl trioxyethylene phosphoric acid diester (sodium salt), stearyl hexaoxybutylene-methyl trioxyethylene phosphoric acid diester (sodium salt), eicosenyl pentaoxybutylene-methyl trioxyethylene phosphoric acid diester (sodium salt), eicosenyl decaoxybutylene-methyl trioxyethylene phosphoric acid diester (sodium salt), docosenyl pentaoxybutylene-methyl trioxyethylene phosphoric acid diester (potassium salt), docosenyl decaoxybutylene-methyl trioxyethylene phosphoric acid diester (sodium salt), ethylcyclohexyl dioxybutylene-methyl trioxyethylene phosphoric acid diester (sodium salt), propylcyclohexyl tetraoxybutylene-methyl trioxyethylene phosphoric acid diester (sodium salt), octylcyclohexyl tetraoxybutylene-methyl trioxyethylene phosphoric acid diester (sodium salt), nonylcyclohexyl pentaoxybutylene-methyl trioxyethylene phosphoric acid diester (sodium salt), stearylcyclohexyl heptaoxybutylene-methyl trioxyethylene phosphoric acid diester (sodium salt), etc.

(III-4) Aliphatic Alcohol Polyoxyethylene-Polyoxypropylene-Aliphatic Alcohol Polyoxyethylene Phosphoric Acid Diester (Salt)

Octyl tetraoxyethylene-monooxypropylene-methyl trioxyethylene phosphoric acid diester (sodium salt), octyl dioxyethylene-monooxypropylene-dioxyethylene-methyl trioxyethylene phosphoric acid diester (sodium salt), dodecyl pentaoxyethylene-monooxypropylene-methyl trioxyethylene phosphoric acid diester (sodium salt), dodecyl dioxyethylene-monooxypropylene-trioxyethylene-methyl trioxyethylene phosphoric acid diester (sodium salt), tridecyl hexaoxyethylene-monooxypropylene-methyl trioxyethylene phosphoric acid diester (sodium salt), tridecyl dioxyethylene-monooxypropylene-tetraoxyethylene-methyl trioxyethylene phosphoric acid diester (sodium salt), stearyl hexaoxyethylene-dioxypropylene-methyl trioxyethylene phosphoric acid diester (potassium salt), stearyl dioxyethylene-dioxypropylene-tetraoxyethylene-methyl trioxyethylene phosphoric acid diester (sodium salt), eicosenyl tetraoxyethylene-monooxypropylene-methyl trioxyethylene phosphoric acid diester (sodium salt), eicosenyl dioxyethylene-monooxypropylene-dioxyethylene-methyl trioxyethylene phosphoric acid diester (sodium salt), eicosenyl nonaoxyethylene-monooxypropylene-methyl trioxyethylene phosphoric acid diester (sodium salt), eicosenyl dioxyethylene-monooxypropylene-heptaoxyethylene-methyl trioxyethylene phosphoric acid diester (sodium salt), docosenyl tetraoxyethylene-monooxypropylene-methyl trioxyethylene phosphoric acid diester (sodium salt), docosenyl dioxyethylene-monooxypropylene-dioxyethylene-methyl trioxyethylene phosphoric acid diester (sodium salt), docosenyl nonaoxyethylene-monooxypropylene—methyl trioxyethylene phosphoric acid diester (sodium salt), docosenyl dioxyethylene-monooxypropylene-heptaoxyethylene-methyl trioxyethylene phosphoric acid diester (sodium salt), ethylcyclohexyl tetraoxyethylene-monooxypropylene—methyl trioxyethylene phosphoric acid diester (sodium salt), propylcyclohexyl tetra-oxyethylene-monooxypropylene-methyl trioxyethylene phosphoric acid diester (sodium salt), octylcyclohexyl hexaoxyethylene-monooxypropylene—methyl trioxyethylene phosphoric acid diester (sodium salt), nonylcyclohexyl hexaoxyethylene-dioxypropylene-methyl trioxyethylene phosphoric acid diester (sodium salt), stearylcyclohexyl hexaoxyethylene-dioxypropylene-methyl trioxyethylene phosphoric acid diester (sodium salt), etc.

Among those listed above, (I) a phosphoric acid monoester (salt) of aliphatic alcohol alkylene oxide adduct (C) and (II) a phosphoric acid diester (salt) of aliphatic alcohol alkylene oxide adduct (C) are preferable; (I-1) aliphatic alcohol polyoxyethylene phosphoric acid monoester (salt), (I-4) aliphatic alcohol polyoxyethylene-polyoxypropylene phosphoric acid monoester (salt), (II-1) aliphatic alcohol poly-oxyethylene phosphoric acid diester (salt), and (II-4) aliphatic alcohol polyoxyethylene-polyoxypropylene phosphoric acid diester (salt) are further preferable; and (I-4) aliphatic alcohol polyoxyethylene-polyoxypropylene phosphoric acid monoester (salt), and (II-4) aliphatic alcohol polyoxyethylene-polyoxypropylene phosphoric acid diester (salt) are particularly preferable.

Although there is no particular limitation on the method for producing the phosphate ester (salt) (D), it is possible to use a method of: phosphorylating the aliphatic alcohol alkylene oxide adduct (C) through a reaction with a phosphorylation agent such as anhydrous phosphoric acid, phosphoric acid, polyphosphoric acid, and/or phosphorus oxychloride; and neutralizing a reaction product with a hydroxide of an alkali metal and/or a quarternary ammonium hydroxide etc. With this method, monoester, diester, and a mixture thereof etc., can be produced.

Reaction of the aliphatic alcohol alkylene oxide adduct (C) and anhydrous phosphoric acid is performed at a reaction temperature of, for example, 30 degrees centigrade to 150 degrees centigrade (preferably 60 degrees centigrade to 130 degrees centigrade; in other words, the upper limit is 150 degrees centigrade, preferably 130 degrees centigrade, and the lower limit is 30 degrees centigrade, preferably 60 degrees centigrade) in a nitrogen atmosphere. When (C) and anhydrous phosphoric acid are reacted at 3:1 (mole ratio), a mixture whose monoester:diester ratio (M/D) is 1:1 (mole ratio) is obtained. Furthermore, the M/D ratio can be controlled by adding water to the reaction system, and monoesters and diesters are produced stoichiometrically in accordance with the amount of added water. When water is added, an M/D ratio larger than 1 is obtained. Furthermore, reaction time is, although it varies depending on the reaction temperature, 1 to 10 hours (preferably, 2 to 5 hours; in other words, the upper limit is 10 hours, preferably 5 hours, and the lower limit is 1 hour, preferably 2 hours). The end point of phosphorylation is a point when an acid value (AV) represented by {56100/(molecular weight of phosphoric acid esterified compound)} is, with respect to the theoretical value, 90 to 110% (preferably 95 to 105%; in other words, the upper limit is 110%, preferably 105%, and the lower limit is 90%, preferably 95%).

It should be noted that, with an ordinarily producing method, highly pure monoesters or diesters cannot be obtained, and its M/D ratio is limited to the mole ratio (stoichiometric ratio) of the material compositions and is determined statistically (random distribution). Although those that are highly pure may be used, it is possible to use a mixture of monoesters and diesters from a standpoint of cost etc. The M/D ratio can be determined through 31P-NMR measurement. More specifically, it can be calculated from an integral value ratio of a signal around 4.9 ppm (monoester) and a signal around 1.0 ppm (diester).

Thereafter, depending on the purpose, it is possible to conduct neutralization thereto (complete neutralization and partial neutralization) using a solution of such as: a hydroxide of an alkali metal such as sodium hydroxide and/or potassium hydroxide; a hydroxide of an alkaline earth metal such as barium hydroxide; and a quarternary ammonium hydroxide.

As the phosphate ester (D), other than that shown by the general formula (1) or (2), a pyrophosphoric acid ester of an aliphatic alcohol of the alkylene oxide adduct (C) or the like can be used. Examples of the pyrophosphoric acid ester include pyrophosphoric acid monoester, pyrophosphoric acid diester, pyrophosphoric acid triester, and pyrophosphoric acid tetraester. When, as the phosphate ester (salt) (D), the compound represented by general the formula (1) or (2), or the pyrophosphoric acid ester is used; the contained amount of the compound represented by the general formula (1) or (2) or the pyrophosphoric acid ester is preferably, based on the mass of (D), 80 to 100 mass %, further preferably 90 to 100 mass %, and particularly preferably 95 to 100 mass %.

As the dispersant, dispersants other than the phosphate ester (salt) (D) may be used, as long as the advantageous effect of the present invention does not deteriorate. As dispersants other than the phosphate ester (salt) (D), those known in the art as a reversed phase suspension polymerization dispersant can be used, and examples thereof include: anionic dispersants (polyoxyethylene alkyl ether sulfate (disclosed in Japanese Patent Publication No. H06-93008); monoalkyl phosphate (disclosed in Japanese Patent Publication No. S61-209201), etc.); and nonionic dispersants (sucrose fatty acid ester, sorbitol fatty acid ester, aliphatic alcohol alkylene oxide adduct, alkyl phenol alkylene oxide adduct, etc.).

As a non-aqueous organic solvent used in reversed phase suspension polymerization, basically, it is possible to use any of those that cannot be easily dissolved in water and are inert to polymerization. Examples of the non-aqueous organic solvent include acyclic aliphatic hydrocarbons having a carbon number of 5 to 12, cyclic aliphatic hydrocarbons having a carbon number of 5 to 12, and aromatic hydrocarbons having a carbon number of 6 to 12. Examples of acyclic aliphatic hydrocarbons include n-pentane, n-hexane, n-heptane, n-octane, and n-dodecane. Examples of cyclic aliphatic hydrocarbons include cyclohexane, methylcyclohexane, and hexylcyclohexane. Examples of aromatic hydrocarbons include benzene, toluene, xylene, and di-ethylbenzene.

There is no particular limitation on a polymerization initiator that can be used for the reversed phase suspension polymerization, and a polymerization initiator known to the public can be used. Examples thereof include azo initiators, peroxide based initiators, redox initiators, and organic halogenated compound initiators. Examples of azo initiators include azobis isobutyronitrile, azobis cyanovaleric acid and salts thereof, 2,2'-azobis(2-amidinopropane) hydrochloride, and 2,2'-azobis(2-methyl-N-(2-hydroxyethyl) propionamide.

Examples of peroxide based initiators include inorganic peroxides (e.g., hydrogen peroxide, ammonium persulfate, potassium persulfate, and sodium persulfate, etc.), and organic peroxides (e.g., benzoyl peroxide, di-t-butyl peroxide, cumene hy-droperoxide, succinic acid peroxide, and di(2-ethoxyethyl) peroxydicarbonate, etc.). Examples of redox initiators include those that are a combination between a reducing agent such as a sulfite or a bisulfite of an alkali metal, ammonium sulfite, ammonium bisulfite, ferric chloride, ferric sulfate and/or ascorbic acid, and an oxidizer such as a persulfate of an alkali metal, ammonium persulfate, hydrogen peroxide and/or an organic peroxide.

As the organic halogenated compound initiators, an organic halogenated compound or the like whose halogen number is 1 to 10 or more and whose carbon number is 1 to 15 or more and that is selected from a group consisting of alkyl halides, halogenated alkyl phenyl ketones, halogenated alkyl carboxylic acids, and halogenated alkyl carboxylic acid alkyl esters is used. Examples thereof include tetrachloromethane, trichlorobromomethane, trichloroiodomethane, dichloro methylphenyl ketone, 1-bromo-1-methylethyl carboxylic acid, and a 1-bromo-1-methylethyl carboxylic alkyl ester whose alkyl group has a carbon number of 1 to 8 (e.g., 1-bromo-1-methylethyl carboxylic acid methyl, 1-bromo-1-methylethyl carboxylic acid ethyl, 1-bromo-1-methylethyl carboxylic acid octyl, and 1-bromo-1-methylethyl carboxylic acid lauryl).

With regard to these initiators, a single type may be used by itself, or a combination of two or more types may be used. Among those described above, azo initiators, redox initiators, and combinations thereof are preferable. When a polymerization initiator is used, usage amount of the polymerization initiator is preferably, based on the total weight of all monomers, 0.005 to 0.5 wt %, further preferably 0.007 to 0.4 wt %, and particularly preferably 0.009 to 0.3 wt %. In other words, in this case, with regard to the usage amount of the polymerization initiator, the upper limit is preferably 0.5 wt %, further preferably 0.4 wt %, and particularly preferably 0.3 wt %, and the lower limit is preferably 0.005 wt %, further preferably 0.007 wt %, and particularly preferably 0.009 wt %.

The monomer can be supplied to the non-aqueous organic solvent directly, or as an aqueous solution. From a standpoint of removing reaction heat, it is preferable to supply an aqueous solution of the monomer. Although supplying of the aqueous solution of the monomer is performed continuously at a constant rate, the supply rate may be altered if desired. Furthermore, supply of the monomer aqueous solution can be momentary interrupted in mid-course. The supply rate of the monomer aqueous solution and the stirring strength are preferably determined such that the monomer aqueous solution is sufficiently dispersed.

If desired, it is possible to premix the monomer solution and the hydrophobic organic solvent, and supply the mixture to the hydrophobic organic solvent maintained under a polymerization condition. The polymerization temperature is, although it depends on the type and usage amount of the polymerization initiator, preferably 40 degrees centigrade to 150 degrees centigrade, and further preferably 60 degrees centigrade to 90 degrees centigrade. In other words, with regard to the polymerization temperature, the upper limit is preferably 150 degrees centigrade and further preferably 90 degrees centigrade, and the lower limit is preferably 40 degrees centigrade and further preferably 60 degrees centigrade. Furthermore, polymerization is preferably conducted while the hydrophobic organic solvent is in reflux. When the temperature exceeds the above described range and becomes too high, self-crosslinking tends to increase and various physical properties (e.g., water absorption performance etc.) of the produced polymer tend to deteriorate. On the contrary, when the temperature falls below the above described range and becomes too low, not only the polymerization time tends to be long, but also unexpected polymerization tends to occur and an aggregate is easily produced.

When supplying the monomer aqueous solution, the monomer concentration in the monomer aqueous solution, i.e., the ratio (total monomer weight/monomer aqueous solution weight) of the weight of total monomer with respect to the weight of the monomer aqueous solution is preferably 10 to 45 wt %, further preferably 12 to 40 wt %, and particularly preferably 15 to 35 wt %. In other words, with regard to the monomer concentration, the upper limit is preferably 45 wt %, further preferably 40 wt %, and particularly preferably 35 wt %, and the lower limit is preferably 10 wt %, further preferably 12 wt %, and particularly preferably 15 wt %. When the monomer concentration is within the above described range, it is efficient when removing water thereafter etc., and the molecular weight distribution of the obtained polymer tends to become narrow since side reactions such as self-crosslinking are unlikely to occur. It should be noted that total monomer refers to all the monomers that are used.

A (crosslinked) polymer obtained through the reversed phase suspension polymerization using the dispersant of the present invention can have the non-aqueous organic solvent removed therefrom, dried, and, if necessary, have a surface crosslinking treatment performed thereon using a surface crosslinking agent. It is preferable to have a crosslinking treatment performed around the surface of particles of the (crosslinked) polymer using a surface crosslinking agent, since, when the polymer is used as a water-absorbent resin, the water absorption velocity increases and the water absorption amount under pressurization also further increases.

The BET specific surface area of the water-absorbent resin powder used in the present invention can be adjusted by, for example, changing as appropriate the conditions of the reversed phase suspension polymerization. Conditions of the reversed phase suspension polymerization may be changed, for example, as follows.

A) Selecting a type of dispersant that is for reversed phase suspension polymerization, or adjusting the amount of the dispersant. Increasing the amount of the dispersant tends to decrease the specific surface area, and reducing the amount of the dispersant tends to increase the specific surface area.

B) Adjusting the conditions at which the solvent (including water) used for the reversed phase suspension polymerization is distilled off. Mildly distilling off the solvent (including water) tends to reduce the specific surface area, whereas rapidly distilling off the solvent (including water) tends to increase the specific surface area. When the solvent (including water) is rapidly distilled off, the specific surface area tends to increase since the solvent escapes rapidly and a large number of voids are generated in the polymer particles to create a so-called pumice stone state.

C) Causing the polymer particles to absorb a solvent consisting of water or a low-boiling point organic-solvent containing solution, and removing the solvent while adjusting the removal condition. For example, the BET specific surface area can be adjusted by: causing the polymer particles to absorb (ordinarily, to absorb 1.2 to 100 times amount thereof, preferably 1.5 to 75 times amount thereof, and particularly preferably 2 to 50 times thereof) water, or a mixed solution of water and a hydrophilic solvent such as methanol, ethanol, and acetone; and removing the absorbed solvent.

As described above, when a solvent (an organic solvent, water, etc.) is used for the polymerization, it is preferred to remove the solvent by distillation after the polymerization. When the solvent contains water as a solvent, the water content (mass %) with respect to the mass (100 mass %) of the crosslinked polymer after the removal by distillation is preferably from 0 mass % to 20 mass %, more preferably from 1 mass % to 10 mass %, even more preferably from 2 mass % to 9 mass %, and most preferably from 3 mass % to 8 mass %. When the water content (% by mass) falls within the above range, the absorbing performance and the breakability of the water-absorbent resin powder after drying become further favorable.

It is noted that the content of the organic solvent and the water content are obtained based on a decrease in the mass of a measurement sample from before heating to after heating by an infrared moisture measuring instrument {JE400 manufactured by Kett Electric Laboratory or the like: 120 plus or minus 5 degrees centigrade, 30 minutes, an atmospheric humidity before heating of 50 plus or minus 10% RH, lamp specifications of 100 V and 40 W}.

As the method for removing the solvent (including water) by distillation, a method in which removal by distillation (drying) is conducted by hot air at a temperature in a range from 80 degrees centigrade to 400 degrees centigrade, a thin film drying method with a drum dryer or the like heated at the temperature in a range from 100 degrees centigrade to 400 degrees centigrade, a (heating) reduced-pressure drying method, a freeze-drying method, a drying method with infrared rays, decantation, filtration, and the like can be used.

The surfaces of the obtained polymer particles are preferably crosslinked with (b) the crosslinking agent. The surface crosslinking is preferably conducted after drying the polymer particles. The surface crosslinking is conducted by, for example, spraying or impregnating the polymer particles with a solution containing the surface crosslinking agent, and then heating the polymer particles at the temperature in a range from 100 degrees centigrade to 200 degrees centigrade.

The crosslinked polymer (A) can be pulverized after being dried, where necessary. The pulverizing method is not particularly limited, and, for example, an ordinary pulverizing apparatus such as a hammer type pulverizer, an impact type pulverizer, a roll type pulverizer, and a jet streaming type pulverizer can be used. The particle size of the pulverized crosslinked polymer (A) can be adjusted by sieving or the like where necessary.

The weight average particle size (micrometer) of the crosslinked polymer (A) that is sieved where necessary is preferably from 50 micrometers to 1000 micrometers, more preferably from 80 micrometers to 700 micrometers, even more preferably from 100 micrometers to 600 micrometers, particularly preferably from 120 micrometers to 500 micrometers, and most preferably from 150 micrometers to 450 micrometers. When the weight average particle size (micrometer) of the crosslinked polymer (A) falls within the above range, the absorbing performance becomes further favorable.

It is noted that the weight average particle size is measured with a ro-tap test sieve shaker and standard sieves (JIS Z8801-1: 2006) according to the method described in Perry's Chemical Engineers Handbook, Sixth Edition (The McGraw-Hill Companies, 1984, Page 21). In other words, as JIS standard sieves, for example, sieves of 1000 micrometers, 850 micrometers, 710 micrometers, 500 micrometers, 425 micrometers, 355 micrometers, 250 micrometers, 150 micrometers, 125 micrometers, 75 micrometers, and 45 micrometers, and a tray are combined in order from above. About 50 g of a measurement particle is placed into the uppermost sieve, and shaken with the ro-tap test sieve shaker for 5 minutes. The weights of the measurement particles on each sieve and the tray are measured, and the weight fraction of the particles on each sieve is obtained with the total weight regarded as 100% by weight. The values are plotted in a log probability paper {the horizontal axis is used for the opening of the sieve (particle size) and the vertical axis is used for the weight fraction}, then a line is drawn so as to connect each point, and a particle size corresponding to 50% by weight of the weight fraction is obtained and regarded as a weight average particle size.

The crosslinked polymer (A) is preferably treated with a surface modifier (B). Examples of the surface modifier (B) include polyvalent metal compounds such as aluminum sulfate, potassium alum, ammonium alum, sodium alum, (poly) aluminum chloride, and hydrates thereof; polycation compounds such as polyethyleneimine, polyvinylamine, and polyallylamine; inorganic fine particles; a surface modifier (B1) containing a hydrocarbon group; a surface modifier (B2) containing a hydrocarbon group having a fluorine atom; and a surface modifier (B3) having a polysiloxane structure.

Examples of the inorganic fine particles include oxides such as silicon oxide, aluminum oxide, iron oxide, titanium oxide, magnesium oxide, and zirconium oxide, carbides such as silicon carbide and aluminum carbide, nitrides such as titanium nitride, and complexes thereof (e.g., zeolite, talc, etc.). Among them, oxides are preferred, and silicon oxide is further preferred. The volume average particle size of the inorganic fine particles is preferably from 10 nm to 5000 nm, more preferably from 30 nm to 1000 nm, even more preferably from 50 nm to 750 nm, and most preferably from 90 nm to 500 nm. It is noted that the volume average particle size is measured in a solvent by a dynamic light scattering method. Specifically, the volume average particle size is measured in cyclohexane as a solvent at a temperature of 25 degrees centigrade by using the nano track particle size distribution measuring instrument UPA-EX150 (light source: He—Ne laser) manufactured by Nikkiso Co., Ltd.

Examples of the surface modifier (B1) containing a hydrocarbon group include polyolefin resins, polyolefin resin derivatives, polystyrene resins, polystyrene resin derivatives, waxes, long-chain fatty acid esters, long-chain fatty acids and salts thereof, long-chain aliphatic alcohols, and mixtures of two or more of them.

Examples of the surface modifier (B2) containing a hydrocarbon group having a fluorine atom include perfluoroalkanes, perfluoroalkanes, perfluoroaryls, perfluoroalkyl ethers, perfluoroalkylcarboxylic acids or salts thereof, perfluoroalkyl alcohols, and mixtures of two or more of them.

Examples of the surface modifier (B3) having a polysiloxane structure include poly-dimethylsiloxane; polyether-modified polysiloxanes such as polyoxyethylene-modified polysiloxane and poly(oxyethylene/oxypropylene)-modified polysiloxane; carboxy-modified polysiloxanes; epoxy-modified polysiloxanes; amino-modified polysiloxanes; alkoxy-modified polysiloxanes; and mixtures thereof.

As the surface modifier (B), in light of absorption properties, the surface modifier (B3) having a polysiloxane structure and inorganic fine particles are preferred, and amino-modified polysiloxanes, carboxy-modified polysiloxanes, and silica are more preferred.

The method for treating the crosslinked polymer (A) with the surface modifier (B) is not particularly limited, as long as treatment is conducted such that the surface modifier (B) is present on the surface of the crosslinked polymer (A). However, from the standpoint that the amount of the surface modifier (B) on the surface is controlled, it is preferred that the surface modifier (B) is mixed with a dried product of the crosslinked polymer (A), not with a water-containing gel of the crosslinked polymer (A) or a polymerization liquid that is prior to polymerization of the crosslinked polymer (A). It is noted that it is preferred that the mixing is uniformly conducted.

The amount of the surface modifier (b) is preferably from 0.001 part by mass to 1 part by mass with respect to 100 parts by mass of the crosslinked polymer (A).

The shape of the water-absorbent resin powder is not particularly limited, and examples thereof include an indefinite crushed shape, a scale shape, a pearl shape, a rice grain shape, a granular shape obtained by aggregating these particles. Among them, the pearl shape, the rice grain shape, or the granular shape obtained by aggregating these particles is preferred from the standpoint that the powder in such a shape can be well entangled with fibrous materials in applications such as a disposable diaper and there is little possibility of the powder falling off from the fibrous materials.

The outer absorbent article of the present invention is an outer absorbent article having an absorbent body formed from at least one layer of an absorption layer, wherein the absorbent body includes a water-absorbent resin powder satisfying the above described requirements of (a) to (d).

The absorbent body of the outer absorbent article of the present invention is composed of at least one absorption layer. The absorption layer includes, for example, the water-absorbent resin powder and a fibrous base material as a water absorption material. It is possible to make the thin absorber, if the water absorption layer consists of the water-absorbent resin powder as the water absorption material. The water absorption layer comprising the fibrous base material is superior in body fluid dispersibility. Examples of the fibrous base material include fiberized pulp, thermal bonding fibers, etc. Examples of the fiberized pulp include pulp fibers known in the art. The thermal bonding fibers are used for enhancing shape-retention. Specific examples of the thermal bonding fibers include fibers of polyolefin such as polyethylene and polypropylene, polyester fibers, and composite fibers. The absorption layer can be obtained by, for example, mixing a granular water-absorbent resin powder and a hydrophilic fiber assembly layer such as pulverized pulp fibers and cellulose fibers, wrapping them using a cover sheet such as a liquid permeable nonwoven fabric sheet or a paper sheet such as a tissue paper, and molding them in a predetermined shape such as a rectangular shape, a hourglass shape, a gourd shape, a battledore shape, and the like.

In the outer absorbent article of the present invention, the absorbent body preferably has, on a skin surface side, the water-absorbent resin powder satisfying the above described requirements of (a) to (d). This is because vapor absorption effect can be further enhanced by having, on the skin surface side, the water-absorbent resin powder satisfying the above described requirements of (a) to (d). From that standpoint, the water-absorbent resin powder satisfying the above described requirements of (a) to (d) is preferably included in the uppermost layer of the absorption layer constituting the absorbent body of the outer absorbent article of the present invention.

The outer absorbent article of the present invention preferably has, for example, a surface sheet material disposed on a skin surface side of the absorbent body and a liquid impermeable exterior sheet material disposed on an external surface side of the absorbent body, wherein at least one part of the surface sheet material is liquid permeable. In the following, the present invention is described based on one embodiment of a diaper outer body (outer absorbent article) to which a urine absorption pad is attached as an inner absorbent article for use.

In one preferable embodiment, the diaper outer body (outer absorbent article) of the present invention includes a liquid permeable top sheet, a liquid impermeable back sheet, an absorbent body interposed between the liquid permeable top sheet and the liquid impermeable back sheet, wherein the absorbent body includes the water-absorbent resin powder satisfying the above described requirements of (a) to (d). In this case, the liquid permeable top sheet corresponds to the surface sheet material, and the liquid impermeable back sheet corresponds to the exterior sheet material. In addition, if necessary, side sheets may be provided on both sides in the width direction of the liquid permeable top sheet. The side sheets are bonded to the upper parts of both side-edge portions in the width direction of the top sheet, and portions of the side sheet inwards of bonding points form one pair of rise flaps along both side edges of the absorbent body.

In another preferable embodiment, the diaper outer body (outer absorbent article) of the present invention comprises a laminated body composed of an inner sheet and an outer sheet, and an absorbent body disposed on a skin surface side of the laminated body between a liquid permeable top sheet and a liquid impermeable back sheet, wherein the absorbent body includes the water-absorbent resin powder satisfying the above described requirements of (a) to (d). In this case, the liquid permeable top sheet corresponds to the surface sheet material, and the laminated body composed of the inner sheet and the outer sheet corresponds to the exterior sheet material. To upper parts of both side-edge portions in the width direction of the liquid permeable top sheet, one pair of rise flaps may be formed along both side edges of the absorbent body.

With respect to the terms of each part of the diaper outer body (outer absorbent article), when a diaper is worn, a portion placed on the abdominal side of a wearer is referred to as a front abdominal portion, a portion placed on the hip side of the wearer is referred to as a back portion, and a portion located between the front abdominal portion and the back portion and placed on the crotch of the wearer is referred to as a crotch portion. A front-back direction of the diaper is a direction from the front abdominal portion to the back portion of the diaper, and the width direction of the diaper is a direction that is on the same surface as the diaper when the diaper is planarly unfolded and that is orthogonal to the front-back direction.

The diaper outer body (outer absorbent article) may be: a pants-type diaper outer body that has a front abdominal portion, a back portion, and a crotch portion located between them, and that has a waist opening and one pair of leg openings formed when the front abdominal portion and the back portion are joined to respective side edges; or an open-type diaper outer body that is used by joining a front abdominal portion and a back portion together with a securing tape or the like. From a standpoint of being able to easily exchange diapers, the diaper outer body of the present invention can be suitably used as an open-type diaper outer body that is used by joining the front abdominal portion and the back portion together with a securing tape or the like.

From a standpoint of preventing leakage, the sheet material forming the outer sheet material is preferably a liquid impermeable or a water-repellent nonwoven fabric, and examples thereof include water-repellent or liquid impermeable nonwoven fabrics (e.g., spunbond nonwoven fabrics, melt-blown nonwoven fabrics, and SMS (span bond-melt blow-span bond) nonwoven fabrics) formed from a hydrophobic fiber (e.g., polypropylene, polyethylene, polyester, polyamide, and nylon), and water-repellent or liquid impermeable plastic films. When a plastic film is used as the exterior sheet material, from a standpoint of improving comfort of the wearer by preventing dampness, a plastic film having moisture permeability (breathability) is preferably used.

The diaper outer body (outer absorbent article) is preferably provided with a waist elastic member along a waist opening edge of the front abdominal portion or the back portion. By having the waist elastic members, leakage of excrement such as urine or the like is unlikely to occur from the back side or the abdominal portion side even when the wearer is lying down. Multiple waist elastic members may be provided.

The diaper outer body (outer absorbent article) is preferably provided with a leg elastic member along a leg opening edge. By having the leg elastic member, leakage of excrement such as urine or the like from the leg opening edge is prevented. It should be noted that the leg opening edge is the edge of the circumference of the leg opening of the diaper outer body. Multiple leg elastic members may be provided.

The diaper outer body (outer absorbent article) is preferably provided with multiple torso circumference elastic members at the front abdominal portion and/or the back portion in the width direction of the diaper main body. By having the torso circumference elastic members, fitting of the diaper at the circumference of the hip and lower abdominal region improves.

As each of the elastic members, an elastic expandable material ordinarily used for disposable diapers can be used, such as polyurethane threads, polyurethane films, natural rubbers, etc. Each of the elastic members is preferably, in a stretched state, fixed to exterior sheet materials and/or surface sheet materials using a hot-melt adhesive. As the hot-melt adhesive, a rubber based hot melt adhesive is preferable.

The surface sheet material whose at least one part is liquid permeable is disposed on the skin surface side of the diaper outer body (outer absorbent article). The surface sheet material of the diaper outer body has a top sheet made of, for example, a nonwoven fabric material. The top sheet made of a nonwoven fabric material has liquid permeability.

The liquid permeable top sheet constituting the surface sheet material of the diaper outer body is suitable for quickly capturing and transferring fluid in excrement of the wearer to the absorbent body interposed between the surface sheet material and the exterior sheet material.

The liquid permeable top sheet is a liquid permeable sheet material, for example, a nonwoven fabric formed from a hydrophilic fiber; and quickly captures and transfers fluid in excrement of the wearer to the absorbent body. Examples of the nonwoven fabric used as the top sheet include point-bond nonwoven fabrics, air-through nonwoven fabrics, spun lace nonwoven fabrics, and spunbond nonwoven fabrics. As the hydrophilic fiber forming these nonwoven fabrics, cellulose, rayon, cotton, and the like are ordinarily used. It should be noted that, as the top sheet, a liquid permeable nonwoven fabric formed from a hydrophobic fiber (e.g., polypropylene, polyethylene, polyester, polyamide, and nylon) whose surface is hydrophilized with a surfactant may be used.

The liquid impermeable side sheets preferably form rise flaps. The rise flaps prevent side-way leakage of urine etc., and quickly transfer fluid in excrement to the absorbent body. On the side sheets made of a nonwoven fabric material, embossing is preferably performed entirely on the side sheets. When the side sheets are entirely embossed, even if the fastening member of the urine absorption pad makes contact with a part of the side sheet, the fastening member is unlikely to engage the side sheets. There is no particular limitation on the type of embossing, and it may be markings, drawings, or patterns such as a line-form, punctiform, etc.

Rise elastic members are preferably provided at end portions (end portion on the wearer side) of the rise flaps. As a result of contractive force by the rise elastic members, the rise flaps that rise on the wearer side are formed to prevent side-way leakage of urine etc.

In the following, although the absorbent article of the present invention will be described with reference to the drawings, the present invention is not limited to the embodiments shown by the drawings.

FIG. 1 to FIG. 3 are schematic sectional views showing preferable embodiments of the absorbent body composed of at least absorption layer and included in the outer absorbent article of the present invention. Absorbent bodies 2 shown in FIG. 1 to FIG. 3 each includes an absorption layer 2a and an absorption layer 2b disposed below the absorption layer 2a. In the absorbent body 2 shown in FIG. 1, the absorption layer 2a includes, as the water absorbent material, only the water-absorbent resin powder 4 satisfying the above described requirements of (a) to (d). The absorption layer 2b includes a conventional water-absorbent resin powder 6 and a fibrous base material 8. In the absorbent body 2 shown in FIG. 2, the absorption layer 2a includes the water-absorbent resin powder 4 satisfying the above described requirements of (a) to (d), and, other than that, the conventional water-absorbent resin powder 6. The absorption layer 2b includes the conventional water-absorbent resin powder 6 and the fibrous base material 8. In the absorbent body 2 shown in FIG. 3, both the absorption layer 2a and the absorption layer 2b include the conventional water-absorbent resin powder 6 and the fibrous base material 8. The absorbent body 2 has the water-absorbent resin powder 4 satisfying the above described requirements of (a) to (d) sprayed on top of the absorption layer 2a. In the embodiments shown in FIG. 1 to FIG. 3, the absorption layer 2a and the absorption layer 2b are each preferably covered with a liquid permeable sheet such as a tissue paper or the like. As shown in FIG. 1 to FIG. 3, vapor absorption effect can be further enhanced when the absorbent body has the water-absorbent resin powder 4 satisfying the above described requirements of (a) to (d) on the skin surface side.

Although absorbent bodies having a two-layer structure are shown in FIG. 1 to FIG. 3, the absorption layer may be a single layer, or may have a multilayer structure with three or more layers.

FIG. 4 is a plan view showing a preferable embodiment of an open-type diaper outer body 1. FIG. 5 is a schematic cross sectional view along line I-I of the open-type diaper outer body in FIG. 4. In the following, the structure of the open-type diaper outer body 1 will be described with reference to FIG. 4 and FIG. 5.

The open-type diaper outer body 1 includes a liquid permeable top sheet 27, an exterior sheet material 11, and the absorbent body 2 interposed between the liquid permeable top sheet 27 and the exterior sheet material 11. Liquid impermeable side sheets 35 are joined to the upper side of both side-edge portions of the liquid permeable top sheet 27. Portions of the side sheets 35 inward of joining points 34 form rise flaps that rise toward the skin of the wearer. Portions of the side sheet outward of the joining points 34 extend outward from side edges of the absorbent body 2 and are joined to the exterior sheet material. The surface sheet material includes the liquid impermeable side sheets 35 and the liquid permeable top sheet 27 located on the skin surface side.

The open-type diaper outer body 1 includes, in a length direction A, a front abdominal portion 3 and a back portion 5, and a crotch portion 7 between the front abdominal portion 3 and the back portion 5. The front abdominal portion 3 makes contact with the abdominal side of the wearer, and the back portion 5 makes contact with the hip side of the wearer. The crotch portion 7 has provided thereon notches 9 formed so as to follow the circumferences of the legs of the wearer, and is formed to have a smaller width than the front abdominal portion 3 and the back portion 5.

The absorbent body 2 extends in the length direction A from the center of the crotch portion 7. The absorbent body 2 has an approximately hourglass shape having wide parts with a large width in a width direction B at positions corresponding to the front abdominal portion 3 and the back portion 5, and a narrow part therebetween.

The absorbent body 2 includes the absorption layer 2a, and the absorption layer 2b disposed below the absorption layer 2a. The absorption layer 2a includes, as a water absorbent material, only the water-absorbent resin powder 4 satisfying the above described requirements of (a) to (d). The absorption layer 2b includes the conventional water-absorbent resin powder 6 and the fibrous base material 8.

On the external surface side of the absorbent body 2, the liquid impermeable exterior sheet material 11 is disposed. The exterior sheet material 11 includes an outer sheet 11a and an inner sheet 11b. The outer sheet 11a is a nonwoven fabric sheet, and the inner sheet 11b is formed from a liquid impermeable resin film.

The open-type diaper outer body 1 has provided thereon a front-side waist elastic member 15 and a back-side waist elastic member 17 along end edges 12 of the exterior sheet material 11. The waist elastic members 15 and 17 are attached between the outer sheet 11a and the inner sheet 11b in a stretched state in the width direction B. Furthermore, one pair of leg circumference elastic members 20 are provided along right and left side edge parts of the exterior sheet material 11. The leg circumference elastic members 20 are attached between the side sheets 35 and the exterior sheet material 11 in a stretched state in the length direction. Through contraction of each of the elastic members, the open-type diaper outer body 1 fits onto the wearer.

As shown in FIG. 5, the side sheets 35 made of a nonwoven fabric material are joined on both side-edge portions in the width direction of the top sheet 27 made of a nonwoven fabric material. Portions of the side sheets 35 inward of the joining points form rise flaps that rise toward the skin of the wearer through contractive force of elastic members 37 attached in the length direction in a stretched state, and act as a barrier for preventing side-way leakage of urine etc. Portions of the side sheets 35 outward of the joining points extend outward from side edges of the absorbent body 2 and are joined to the exterior sheet material 11.

A securing sheet 36 is provided on the external surface side of the front abdominal portion 3, and one pair of fastening members 38 extending outward are provided on both side-edge portions of the back portion 5. On the fastening members 38, securing elements 40 for detachably engaging the securing sheet 36 are provided. By having the securing elements 40 engage the securing sheet 36, the diaper outer body 1 can be worn by the wearer in a detachable manner. As the securing elements 40, for example, a hook member of a hook-and-loop fastener is suitable. As the securing sheet 36, for example, a loop member of a hook-and-loop fastener is suitable. End portions of inward sides of the fastening members 38 are joined to the diaper outer body 1 with an adhesive in a state of being sandwiched between the side sheets 35 and the exterior sheet material 11.

FIG. 6 shows one example of a pants-type diaper outer body (outer absorbent article) (expansion plan). A pants-type diaper outer body 1 includes the front abdominal portion 3 and the back portion 5 in the length direction A, and the crotch portion 7 between the front abdominal portion 3 and the back portion 5. The front abdominal portion 3 makes contact with the abdominal side of the wearer, and the back portion 5 makes contact with the hip side of the wearer. The crotch portion 7 has provided thereon the notches 9 so as to follow the circumference of the legs of the wearer. In the pants-type diaper outer body 1 in FIG. 6, side edges 3a of the front abdominal portion 3 are joined to side edges 5a of the back portion 5 to form the pants-type diaper outer body 1 having a waist opening and one pair of leg openings.

In the pants-type diaper outer body 1, an absorbent main body 13 is attached on the skin surface side of the exterior sheet material 11. The absorbent main body 13 extends in the length direction A from the center of the crotch portion 7.

On the pants-type diaper outer body 1, the front-side waist elastic member 15 and the back-side waist elastic member 17 are attached in a stretched state in the width direction B along the end edges 12 of the exterior sheet material 11. In addition, front-side leg elastic members 19 and back-side leg elastic members 21 are attached along the notches 9 in a stretched state. On the front abdominal portion 3 and the back portion 5, a front-side torso circumference elastic member 23 and a back-side torso circumference elastic member 25 are respectively attached in the width direction B in a stretched state between the waist elastic member and the leg elastic member. Through contraction of each of the elastic members, the pants-type diaper outer body 1 fits onto the wearer.

FIG. 7 is a schematic cross sectional view along line I-I of the pants-type diaper outer body in FIG. 6. The structure of the pants-type diaper outer body 1 will be described with reference to FIG. 7. The exterior sheet material 11 includes the outer sheet 11a and the inner sheet 11b, and, between both of the sheets, the waist elastic members 15 and 17, the leg elastic members 19 and 21, the torso circumference elastic members 23 and 25 attached in a stretched state. The outer sheet 11a is longer than the inner sheet 11b in the length direction, and has formed thereon folded portions 14 that are folded toward inner surface sides (skin surface side) at the end edges 12.

The absorbent main body 13 is attached on the skin surface side of the exterior sheet material 11. The absorbent main body 13 includes the absorbent body 2 (2a, 2b), the top sheet 27 made of a nonwoven fabric material and disposed on the skin surface side of the absorbent body 2, and a liquid impermeable back sheet 29 provided on the external surface side of the absorbent body 2. On the pants-type diaper outer body 1, a front-side end holding sheet 31 and a back-side end holding sheet 33 are provided so as to cover end portions in the length direction of the absorbent main body 13 at the front abdominal portion 3 and the back portion 5 on the inner surface of the inner sheet 11b.

The absorbent body 2 includes the absorption layer 2a, and the absorption layer 2b disposed below the absorption layer 2a. The absorption layer 2a includes, as the water absorbent material, only the water-absorbent resin powder 4 satisfying the above described requirements of (a) to (d).

The absorption layer 2b includes the conventional water-absorbent resin powder 6 and the fibrous base material 8.

FIG. 8 is a schematic cross sectional view along line II-II of the pants-type diaper outer body in FIG. 7. As shown in FIG. 8, the side sheets 35 made of a nonwoven fabric material are joined on both side-edge portions in the width direction of the top sheet 27 made of a nonwoven fabric material. The side sheets 35 form rise flaps that rise toward the skin of the wearer through contractive force of the elastic members 37 attached in the length direction in a stretched state, and act as a barrier for preventing side-way leakage of urine etc. The liquid impermeable back sheet 29 is rolled upward of the absorbent body 2 and joined to the lower side of both side-edge portions in the width direction of the top sheet 27. By employing such a configuration, excrement such as urine absorbed by the absorbent body 2 is prevented from leaking outward.

The inner absorbent article that can be used in the present invention will be described. With regard to the inner absorbent article that can be used in the present invention, the inner absorbent article is not limited, as long as it can be exchangeably attached to the outer absorbent article and is capable of absorbing body fluid such as urine. Examples of the inner absorbent article include urine absorption pads. In the following, the inner absorbent article that can be used in the present invention will be described on an embodiment of a urine absorption pad.

The urine absorption pad includes, for example, a liquid permeable top sheet, a liquid impermeable back sheet, and an absorbent body interposed between the two sheets. The shape of the urine absorption pad is preferably an approximately rectangular shape having two long side edges and two short side edges. In addition, the urine absorption pad may be provided with one pair of rise flaps extending in the length direction along the two long side edges. The rise flaps prevent side-way leakage of urine etc., and quickly transfer fluid in excrement to the absorbent body. For example, the rise flaps may be provided on both sides in the width direction of the top surface of the absorbent body, or may be provided outside of the side edges of the absorbent body. The rise flaps may be formed by causing inward edges of side sheets provided on both sides in the width direction of the top sheet to rise. Elastic members are preferably provided on free ends (inward edges) of the rise flaps, such that the rise flaps rise toward the skin of the wearer through contractive force of the elastic member.

FIG. 9 and FIG. 10 show one example of a urine absorption pad. FIG. 9 is a plan view from the skin surface side. FIG. 10 is a cross sectional view along line I-I in FIG. 9.

An absorption pad 50 mainly includes a liquid permeable top sheet 51, a liquid impermeable back sheet 53, and an absorbent body 55 interposed between the two sheets. The absorbent body 55 is joined to the top sheet 51 and the back sheet 53 using a hot-melt adhesive or the like, and flap portions of the top sheet 51 and the back sheet 53 extending outward of the absorbent body 55 are joined together using an adhesive or the like. As a result, the absorbent body 55 and excrement such as urine absorbed by the absorbent body 55 are held so as not to leak outward. In the example in FIG. 9 and FIG. 10, the back sheet 53 is rolled upward of the absorbent body 55 to cover width-direction side edges 57 of the absorbent body 55. This is a measure for further firmly holding the absorbent body 55 and excrement such as urine absorbed by the absorbent body 55 so as not to leak outward.

The width of the top sheet 51 is configured to be smaller than the width of the absorption pad 50, and, the lower surfaces of both side-edge portions of the top sheet 51 are joined to upper surfaces of the back sheet 53 slightly outward of fold edges 61 via first jointing parts 63. Side sheets 65 are joined and arranged outward of the top sheet 51 in the width direction. Portions on lower surfaces of the side sheets 65 slightly outward of first fold edges 67 are joined to the upper surface of the top sheet 51 via second joining parts 75. It should be noted that other lower surfaces of the side sheets 65 are also joined onto the upper surface of the top sheet 51 or the upper surface of the back sheet 53 that is folded (not shown). Portions of the side sheets 65 inward of the second joining parts 75 form rise flaps 73 that rise toward the skin of the wearer through contractive force of elastic members 71 that are joined in a stretched state.

The rise flaps 73 are folded outward of the first fold edges 67, and then folded inward at second fold edges 68, and subsequently folded inward at third fold edges 69 so as to cover the elastic members 71. The elastic members 71 are attached inside the third fold edges 69 in a stretched state. The rise flaps 73 are fixed to the vicinity of end edges in the length direction A of the urine absorption pad 50 in a folded state. Since portions of the rise flaps 73 between the fixed portions are not fixed, they rise toward the skin of the wearer through contractive force of the elastic members 71. Since the rise flaps 73 rise mainly at the crotch part of the wearer, side-way leakage of excrement such as urine can be prevented at the crotch part.

As the elastic members 71, stretch materials such as polyurethane thread and natural rubber sheets can be used. With regard to bonding the materials, bonding with a hot-melt adhesive, or thermal bonding is employed.

On the absorption pad 50, securing members 59 are provided on the rear surface side of the back sheet 53. Here, the rear surface side refers to the lower side (lower side in direction C) when viewed in FIG. 10, and is a side that faces the inner surface of the diaper outer body. The upper side viewed in FIG. 10 (upper side in direction C) is a side that faces the skin of the wearer.

Preferably, a hook-and-loop fastener having a hook member is used as the securing members 59. The hook member is preferably flexible and thin made of a plastic member such as polyethylene and polypropylene, and preferably has multiple hook members aligned and standing on a base material sheet that becomes a base.

The securing members 59 including the hook member are attached to the rear surface of the back sheet 53 such that the hook member faces the inner surface of the diaper outer body. The absorption pad 50 is attached to the diaper outer body by allowing the hook member to engage with the inner surface of the diaper outer body. If the hook member is used as the securing member, attaching can be conducted repeatedly, position adjustment can be made easily, and damaging the inner surface of the diaper outer body is unlikely to occur.

The embodiment of attaching the absorption pad 50 to the diaper outer body 1 will be described with reference to FIG. 11 and FIG. 12. As shown in FIG. 11, the absorption pad 50 is folded in two at a twofold part 77, and in a state of being folded in two, is attached to inner surfaces of the unfold-type diaper outer body 1. FIG. 12 is a schematic cross-sectional view of a situation where the absorption pad 50 is overlaid on the open-type diaper outer body 1. The securing members 59 provided on the rear surface of the back sheet 53 of the absorption pad 50 engage with the top sheet 27 formed from a nonwoven fabric material.

EXAMPLES

In the following, the present invention will be described in detail by means of Examples. However, the present invention is not limited to the following examples, and changes and embodiments that do not depart from the essence of the present invention are also included in the scope of the present invention.

(Water-absorbent Resin Powder Evaluation Method)

(a) Specific Surface Area Measured by BET Multipoint Method

A water-absorbent resin powder used for specific surface area measurement was dried in a vacuum dryer under reduced pressure of approximately 1 Pa at a temperature of 100 degrees centigrade for 24 hours. Then, by using a high-precision fully-automatic gas absorber (product name: BELSORP36, manufactured by BEL Japan, Inc.), an adsorption isothermal line was measured at a temperature of 77 K with a method using krypton gas as an adsorption gas to obtain a specific surface area from a multipoint BET plot.

(b) Vapor Blocking Ratio (Range 0% to 0.90%)

10 g of the water-absorbent resin powder that is to be measured was uniformly placed in a 5 cm-diameter plate made of aluminum, and left still for 2 hours in a constant temperature-and-humidity chamber of 50 degrees centigrade at a relative humidity of 80% RH. After being left still for 2 hours, the mass of the measuring sample was measured, and the sample was gently sieved using a 12-mesh wire net. The mass of a powdered object of the measuring sample that has not passed the 12-mesh due to blocking caused by moisture absorption was measured, and a moisture absorption blocking ratio was obtained from the following formula.

(Vapor blocking ratio)=ON×100/TOT

Here, ON represents the weight of the measuring sample left on the 12-mesh net after being left still for 2 hours, and TOT represents the total mass of the measuring sample after being left still for 2 hours.

(c) Absorption Ratio 1 g of the water-absorbent resin powder that is to be measured was placed in a bag-form tea bag (10 cm×20 cm) made of a nylon textile having a sieve-opening of 57 micrometers (255-mesh), and the opening of the tea bag was heat sealed. Next, 1 liter of 0.9 mass % saline solution was poured in a beaker having a capacity of 1 liter, and the tea bag was immersed therein for 1 hour. After the immersion, the tea bag was hung for 10 minutes to remove excessive water, and the total weight ($F1$) was measured. On the other hand, as a blank, the weight ($F0$) of a tea bag not having placed therein the water-absorbent resin and having performed thereon the same operation was measured. The weight difference of the two was obtained as a water absorption amount (g), and this numerical value was used to obtain an absorption ratio (g/g) of the water-absorbent resin powder.

Absorption ratio (g/g)=($F1$–$F0$)/Sample mass (d) Water Retention Amount

The tea bag obtained from the above described water absorption capacity measurement was placed in a basket type centrifugal dehydrator having a diameter of 30 cm, dehydrated at 1000 rpm (centrifugal force: 167 G) for 90 seconds, and then its total weight ($R1$) was measured. On the other hand, as a blank, the weight ($R0$) of a tea bag not having placed therein the water-absorbent resin and having performed thereon the same operation was measured. The weight difference of the two was obtained as the weight (g) of the 0.9 wt % saline solution retained in the water-absorbent resin powder, and this numerical value was used to obtain a water retention amount (g/g) of the water-absorbent resin.

Water retention amount (g/g)=($R1$–$R0$–Sample mass)/Sample mass (Production Examples of Dispersant for Reversed Phase Suspension Polymerization)

<Dispersant Production Example 1>

In a stainless steel autoclave having stirring and temperature adjusting functions, 186 parts by mass (1 mole) of lauryl alcohol, 0.32 parts by mass of magnesium perchlorate, and 0.03 parts by mass of magnesium hydroxide were added. The obtained mixture system was nitrogen-substituted, and dehydrated under reduced pressure (20 mmHg) for 1 hour at 120 degrees centigrade. Next, 88 parts by mass (2 mole) of ethylene oxide (EO) was introduced therein at 150 degrees centigrade such that the gage pressure becomes 0.1 MPa to 0.3 MPa to obtain a lauryl alcohol EO adduct (A1). Next, 279 parts by mass (1.02 mol) of the EO adduct (A1), 50.1 parts by mass (0.353 mole) of anhydrous phosphoric acid, and 1.058 parts by mass (0.0588 mole) of water were charged in a glass container, and allowed to react at 65 degrees centigrade for 8 hours to obtain a dispersant (B1) that is a phosphate ester and whose M/D showing a proportion of monoester/diester is 1.4.

<Dispersant Production Example 2>

274 parts by mass (1 mol) of the lauryl alcohol EO adduct (A1) obtained similarly to Production Example 1 was mixed with 1.3 parts by mass of potassium hydroxide, and the mixture was allowed to react with 44 parts by mass (1 mole) of ethylene oxide (EO) at 130 degrees centigrade to obtain a lauryl alcohol EO adduct (A2). Next, 324 parts by mass (1.02 mole) of the EO adduct (A2), 50.1 parts by mass (0.353 mol) of anhydrous phosphoric acid, and 1.058 parts by mass (0.0588 mol) of water were charged in a glass container, and allowed to react at 65 degrees centigrade for 8 hours to obtain a dispersant (B2) that is a phosphate ester and whose M/D is 1.4.

<Dispersant Production Example 3>

In a glass reaction container having a stirrer, a thermometer, a reflux condenser, and a nitrogen introduction pipe; 45.2 parts by mass (1.13 mole) of sodium hydroxide was dissolved in 811 parts by mass of water. 330 parts by mass of the phosphate ester (B2) obtained similarly to Production Example 2 was added thereto at 60 degrees centigrade to obtain an approximately 30 mass % solution of a dispersant (B3) that is a phosphoric acid ester sodium salt.

(Water-absorbent Resin Powder Synthesis Examples)

<Water-absorbent Resin Powder Synthesis Example 1>

While cooling a mixture of 207.7 parts by mass of acrylic acid and 13.5 parts by mass of water at 30 to 20 degrees centigrade, 346.2 parts by mass of a 25 mass % sodium hydroxide solution was added thereto. To the produced solution, 0.05 parts by mass of potassium persulfate and 0.008 parts by mass of sodium hypophosphite were added to prepare a monomer solution. Next, 624 parts by mass of cyclohexane was added to a 4-neck flask having a stirrer, a reflux condenser, a thermometer, and a nitrogen gas introduction pipe. 1.56 parts by mass of the dispersant (B1) which is a phosphate ester was added thereto to be dissolved, nitrogen gas was introduced while stirring the mixture at 400 rpm, and the mixture was heated up to 70 degrees centigrade. While maintaining the temperature at 70 degrees centigrade, the prepared monomer solution was dripped therein for 6 minutes at 6.6 parts by mass/minute. After dripping, the mixture was maintained at 75 degrees centigrade for 15 minutes, and then dripping was conducted for 54 minutes at 6.6 parts by mass/minute. Then, the mixture was matured for 30 minutes at 75 degrees centigrade. Next, water was removed through azeotropy with cyclohexane until the water content of the resin became approximately 20% (measured by an infrared moisture meter (model FD-100, manufactured by Kett Electric Laboratory). When the mixture was cooled to 30 degrees centigrade and stirring was stopped, resin particles settled, and therefore the resin particles and cyclohexane were separated by decantation.

80 parts by mass of the obtained resin particles and 140 parts by mass of cyclohexane were added to an eggplant-shaped flask. Then, 3.4 parts by mass of a cyclohexane solution containing 0.35 mass % of glycerin poly glycidyl ether (Nagase Kasei Kougyou Co. Ltd., product name: DENACOL EX-314) was added thereto and the mixture was heated to 60 degrees centigrade and held for 30 minutes. Then, the mixture was further heated and held under reflux of cyclohexane for 30 minutes. Next, the mixture was filtrated to acquire resin particles, and dried under reduced pressure at 80 degrees centigrade to obtain a crosslinked polymer (C-1). 100 parts by mass of the resin particles of the obtained crosslinked polymer (C-1), 0.2 parts by mass of silica (manufactured by Toshin Chemicals Co., Ltd., Aerosil 380), and 0.02 parts by mass of carboxy modified polysiloxane (manufactured by Shin-Etsu Chemical Co., Ltd., X-22-3701E) were mixed and stirred at 85 degrees centigrade for 60 minutes to obtain a water-absorbent resin powder 1.

<Water-absorbent Resin Powder Synthesis Example 2>

Except for using the dispersant (B2) that is a phosphate ester instead of the dispersant (B1) that is a phosphate ester, a water-absorbent resin powder 2 was obtained similarly to Synthesis Example 1.

<Water-absorbent Resin Powder Synthesis Example 3>

Except for using the dispersant (B3) that is a phosphoric acid ester sodium salt instead of the dispersant (B1) that is a phosphate ester, a water-absorbent resin powder 3 was obtained similarly to Synthesis Example 1.

<Water-absorbent Resin Powder Synthesis Example 4>

Except for changing 3.4 parts by mass to 1.7 parts by mass regarding the cyclohexane solution containing 0.35 mass % of glycerin poly glycidyl ether (Nagase Kasei Kougyou Co. Ltd., product name: DENACOL EX-314), a water-absorbent resin powder 4 was obtained similarly to Synthesis Example 3.

<Water-absorbent Resin Powder Synthesis Example 5>

Except for changing 0.02 parts by mass to 0.006 parts by mass regarding carboxy modified polysiloxane (manufactured by Shin-Etsu Chemical Co., Ltd., X-22-3701E), a water-absorbent resin powder 5 was obtained similarly to Synthesis Example 3.

<Water-absorbent Resin Powder Synthesis Example 6>

A mixture of 200 parts by mass of methanol and 300 parts by mass of water was added to 100 parts by mass of a polyacrylic based water-absorbent resin powder Sanwet IM-930 (San-Dia Polymers, Ltd.) to be absorbed. The produced gel-like material was placed in an autoclave and heated up to 120 degrees centigrade in a sealed state. Then, in a heated state (80 to 120 degrees centigrade), methanol and water were removed from the material under reduced pressure to obtain a water-absorbent resin powder 6.

<Comparative Water-absorbent Resin Powder Synthesis Example 1>

Except for changing 0.2 parts by mass of silica (manufactured by Toshin Chemicals Co., Ltd., Aerosil 380) and 0.02 parts by mass of carboxy modified polysiloxane (manufactured by Shin-Etsu Chemical Co., Ltd., X-22-3701E) to 0.04 parts by mass of silica (manufactured by Toshin Chemicals Co., Ltd., Aerosil 380) and 0.006 parts by mass of carboxy modified polysiloxane (manufactured by Shin-Etsu Chemical Co., Ltd., X-22-3701E); a comparative water-absorbent resin powder 1 was obtained similarly to Water-absorbent Resin Powder Synthesis Example 3.

<Comparative Water-absorbent Resin Powder Synthesis Example 2>

Except for changing 3.4 parts by mass to 6.8 parts by mass regarding the cyclohexane solution containing 0.35 mass % of glycerin poly glycidyl ether (Nagase Kasei Kougyou Co. Ltd., product name: DENACOL EX-314); a comparative water-absorbent resin powder 2 was obtained similarly to Water-absorbent Resin Powder Synthesis Example 3.

<Comparative Water-absorbent Resin Powder Synthesis Example 3>

The polyacrylic based water-absorbent resin powder Sanwet IM-930 was used as a comparative water-absorbent resin powder 3.

<Comparative Water-absorbent Resin Powder Synthesis Example 4>

100 parts by mass of the polyacrylic based water-absorbent resin powder Sanwet IM-930 (San-Dia Polymers, Ltd.), 0.2 parts by mass of silica (manufactured by Toshin Chemicals Co., Ltd., Aerosil 380), and 0.02 parts by mass of carboxy modified polysiloxane (manufactured by Shin-Etsu Chemical Co., Ltd., X-22-3701E) were mixed and stirred at 85 degrees centigrade for 60 minutes to obtain a comparative water-absorbent resin powder 4.

Characteristics of the obtained water-absorbent resin powders are shown in Table 1.

TABLE 1

| | Water-Absorbent Resin Powder Characteristics | | | |
|---|---|---|---|---|
| | Specific Surface Area by BET Multipoint Method ($m^2/g$) | Vapor Blocking Ratio (%) | Water Retention Amount (g/g) | Absorption ratio (g/g) |
| Water-Absorbent Resin Powder 1 | 0.179 | 0 | 35 | 60 |
| Water-Absorbent Resin Powder 2 | 0.103 | 0 | 36 | 61 |
| Water-Absorbent Resin Powder 3 | 0.039 | 0 | 37 | 62 |
| Water-Absorbent Resin Powder 4 | 0.042 | 0 | 55 | 68 |
| Water-Absorbent Resin Powder 5 | 0.043 | 0.87 | 37 | 60 |
| Water-Absorbent Resin Powder 6 | 0.041 | 0 | 32 | 57 |

TABLE 1-continued

| | Water-Absorbent Resin Powder Characteristics | | | |
|---|---|---|---|---|
| | Specific Surface Area by BET Multipoint Method ($m^2/g$) | Vapor Blocking Ratio (%) | Water Retention Amount (g/g) | Absorption ratio (g/g) |
| Comparative Water-Absorbent Resin Powder 1 | 0.042 | 1.23 | 37 | 61 |
| Comparative Water-Absorbent Resin Powder 2 | 0.040 | 0 | 18 | 38 |
| Comparative Water-Absorbent Resin Powder 3 | 0.033 | 2.98 | 33 | 55 |
| Comparative Water-Absorbent Resin Powder 4 | 0.035 | 0 | 33 | 56 |

(Manufacturing of Absorbent Article)

(a) Outer Absorbent Article

The water-absorbent resin powders 1 to 6 and comparative water-absorbent resin powders 1 to 4 were each mixed with pulverized pulp at a ratio of water-absorbent resin powder:pulverized pulp=1:3 to form absorbent bodies in a sheet form. By using the absorbent bodies formed in a sheet form, outer absorbent articles (diaper exterior bodies) were manufactured. The following were used as sheet materials included in the outer absorbent articles.

(Skin surface side) surface sheet material: D-02220 manufactured by Fukusuke Kogyo Co., Ltd.

(External surface side) exterior sheet material: CFY6020A2A manufactured by Mitsubishi Plastics Industries, Ltd.

(b) Inner Absorbent Article

Water-absorbent resin powders in a crushed form were each mixed with pulverized pulp at a ratio of 1:2 to form absorbent bodies in a sheet form. By using the absorbent bodies in a sheet form, inner absorbent articles (pad-type paper diapers) were manufactured. The following were used as sheet materials included in the inner absorbent articles.

Skin surface side sheet: TA-LSW-18-205-6500 manufactured by Fukusuke Kogyo Co., Ltd.

External surface side sheet: TUKI BS PM-18-320-62/1G SARA-B (moisture permeable) manufactured by Tokuyama Corp.

(Condensation Human Test)

FIG. 13 is an illustrative diagram showing a general outline of a condensation human test. An inner absorbent article (absorption pad) 50 was disposed inside an outer absorbent article 1, and the inner absorbent article (absorption pad) 50 was caused to absorb 450 mL of a saline solution 80. The outer absorbent article 1 was folded in two such that vapor will not escape outside the outer absorbent article 1, and end portions of the outer absorbent article 1 were sealed using a tape 81. After keeping it in a 40 degrees centigrade environment for 3 hours, the inner absorbent article (absorption pad) 50 was taken out. A sensory evaluation was performed regarding the dryness of the surface of the absorbent body of the outer absorbent article placed in the above described environment. 20 adult testers were asked to touch the surface of the absorbent body, and the degree of wetness-feel of the surface was graded in a five point scale of 1 to 5 shown below.

«Grades»

1: Dry

2: Slightly moist but dry

3: Feels slightly moist

4: Feels moist

5: Moist enough to wet the hand (Post-moisture-absorption Absorption-velocity Test)

In a manner similar to the condensation human test shown in FIG. 13, an outer absorbent article that has absorbed moisture was prepared. That is, the inner absorbent article (absorption pad) 50 was disposed inside the outer absorbent article 1, and the inner absorbent article (absorption pad) 50 was caused to absorb 450 mL of the saline solution 80. The outer absorbent article 1 was folded in two such that vapor will not escape outside the outer absorbent article 1, and end portions of the outer absorbent article 1 were sealed using the tape 81. After keeping it in a 40 degrees centigrade environment for 3 hours, the inner absorbent article (absorption pad) 50 was taken out. The outer absorbent article was mounted on a transparent silicon doll-type simulated urination apparatus, and, for a single injection, 150 mL of the saline solution was injected from an urination opening part of the doll-type simulated urination apparatus. At the third injection, the velocity at which liquid disappears from the surface from the start of the injection was measured, and classified into the following ranges.

(Classification)

Poor (P): Not less than 15 seconds

Fair (F): From 5 seconds to less than 15 seconds

Good (G): Less than 5 seconds

Evaluation results of the obtained absorbent articles are shown in Table 2.

TABLE 2

| | Water-Absorbent Resin Powder | Human Test (Grades) | Post-moisture-absorption absorption-velocity Test (Grades) |
|---|---|---|---|
| Example 1 | Water-Absorbent Resin Powder 1 | 2.3 | Good |
| Example 2 | Water-Absorbent Resin Powder 2 | 2.5 | Good |
| Example 3 | Water-Absorbent Resin Powder 3 | 2.7 | Good |
| Example 4 | Water-Absorbent Resin Powder 4 | 2.5 | Good |
| Example 5 | Water-Absorbent Resin Powder 5 | 2.9 | Good |
| Example 6 | Water-Absorbent Resin Powder 6 | 2.7 | Good |

TABLE 2-continued

| | Water-Absorbent Resin Powder | Human Test (Grades) | Post-moisture-absorption absorption-velocity Test (Grades) |
|---|---|---|---|
| Comparative Example 1 | Comparative Water-Absorbent Resin Powder 1 | 3.8 | Fair |
| Comparative Example 2 | Comparative Water-Absorbent Resin Powder 2 | 2.9 | Poor |
| Comparative Example 3 | Comparative Water-Absorbent Resin Powder 3 | 4.2 | Fair |
| Comparative Example 4 | Comparative Water-Absorbent Resin Powder 4 | 4.1 | Good |

As can be understood from Table 2, the outer absorbent articles of Examples 1 to 6 have excellent dryness and absorption velocity when compared to the outer absorbent articles of Comparative Examples 1 to 4. This is thought to be because, by having the absorbent bodies which include the water-absorbent resin powder satisfying the requirements of (a) to (d), vapor escaped from inside the inner absorbent article does not form condensation on the inner surface of the outer absorbent article, resulting in excellent dryness. Furthermore, even in a state where vapor has escaped from inside the inner absorbent article to the inner surface of the outer absorbent article, it is assumed that excellent absorption velocity can be obtained since the absorption characteristics will not deteriorate. On the other hand, the outer absorbent articles of Comparative Examples 1 to 4 have poor results when compared to the outer absorbent articles of the present invention.

In Comparative Example 1, there were cases where the water-absorbent resin powder included in the absorbent body was easily blocked due to vapor. Condensation due to vapor escaped from inside the inner absorbent article was unlikely to be suppressed from forming at the inner surface of the outer absorbent article. Therefore, it is estimated that the human-evaluated dryness and post-moisture-absorption absorption velocity were poor. In Comparative Example 2, there were cases where water retention amount and absorption ratio of the water-absorbent resin powder included in the absorbent body were low. It became difficult to repeatedly absorb large amount of liquid. Therefore, it is estimated that the post-moisture-absorption absorption velocity was poor. In Comparative Example 3, there were cases where specific surface area obtained by BET multipoint method of the water-absorbent resin powder included in the absorbent body was small, and where blocking occurred easily due to vapor. Condensation due to vapor escaped from inside the inner absorbent article was unlikely to be suppressed from forming at the inner surface of the outer absorbent article. Therefore, it is estimated that the human-evaluated dryness and post-moisture-absorption absorption velocity were poor. In Comparative Example 4, there were cases where specific surface area obtained by BET multipoint method for the included water-absorbent resin powder was small. Condensation due to vapor escaped from inside the inner absorbent article was unlikely to be suppressed from forming at the inner surface of the outer absorbent article. Therefore, it is estimated that the human-evaluated dryness was poor.

The present invention includes the following embodiments.

<Embodiment 1>

An outer absorbent article comprising an absorbent body composed of at least one absorption layer, wherein the absorbent body includes a water-absorbent resin powder satisfying following requirements of (a) to (d).

(a) Specific surface area measured by BET multipoint method: $0.040 \text{ m}^2/\text{g}$ to $0.200 \text{ m}^2/\text{g}$ (b) Vapor blocking ratio: 0% to 0.90%

(c) Absorption ratio: 30 g/g to 70 g/g (d) Water retention amount: 20 g/g to 60 g/g <Embodiment 2>

The outer absorbent article according to embodiment 1, wherein the absorbent body includes the water-absorbent resin powder satisfying the requirements of (a) to (d) on a skin surface side.

<Embodiment 3>

The outer absorbent article according to embodiment 1 or 2, wherein an uppermost layer of the absorption layer includes the water-absorbent resin powder satisfying the requirements of (a) to (d).

<Embodiment 4>

The outer absorbent article according to any one of embodiments 1 to 3, comprising a surface sheet material disposed on a skin surface side of the absorbent body and a liquid impermeable exterior sheet material disposed on an external surface side of the absorbent body, wherein at least one part of the surface sheet material is liquid permeable.

<Embodiment 5>

The outer absorbent article according to any one of embodiments 1 to 4, wherein the outer absorbent article is an open-type or pants-type diaper outer body.

<Embodiment 6>

An absorbent article comprising the outer absorbent article according to any one of embodiments 1 to 5, and an inner absorbent body attached to an inner side of the outer absorbent article.

INDUSTRIAL APPLICABILITY

The present invention can be suitably used as, for example, an outer absorbent article, and an absorbent article formed by attaching an inner absorbent article to an outer absorbent article.

REFERENCE SIGNS LIST

1: diaper outer body (outer absorbent article), 2: absorbent body, 3: front abdominal portion, 4: water-absorbent resin powder satisfying requirements of (a) to (d), 5: back portion, 6: water-absorbent resin powder, 7: crotch portion, 8: fibrous base material, 9: notch, 11: exterior sheet material, 12: end edge, 13: absorbent main body, 15: front-side waist elastic member, 17 back-side waist elastic member, 19 front-side leg elastic member, 21: back-side leg elastic member, 23 front-side torso circumference elastic member, 25: back-side torso circumference elastic member, 27: liquid permeable top sheet, 29: liquid impermeable back sheet, 31: front-side end holding sheet, 33: back-side end holding sheet, 34:

joining part, 35: side sheet, 37: elastic member, 50: absorption pad, 51: liquid permeable top sheet, 53: liquid impermeable back sheet, 55: absorbent body, 57: width-direction side edge, 59: securing member, 61: fold edge, 63: first joining part, 65: side sheet, 67: first fold edge, 68: second fold edge, 69: third fold edge, 71: elastic member, 73: rise flap, 75: second joining part, 80: saline solution, 81: tape

The invention claimed is:

1. An outer absorbent article combined with an inner absorbent article, wherein the outer absorbent article comprises an absorbent body composed of at least one absorption layer, wherein the absorbent body includes a water-absorbent resin powder satisfying following requirements of (a) to (d),
    (a) Specific surface area measured by BET multipoint method: 0.040 m$^2$/g to 0.200 m$^2$/g,
    (b) Vapor blocking ratio: 0% to 0.90%,
    (c) Absorption ratio: 30 g/g to 70 g/g, and
    (d) Water retention amount: 20 g/g to 60 g/g;
    when (b) the vapor blocking ratio is measured as follows:
        10g of the water-absorbent resin powder is uniformly placed in a 5 cm-diameter plate made of aluminum, and left still for 2 hours in a constant temperature-and-humidity chamber of 50 degrees centigrade at a relative humidity of 80% RH, afterward the mass (TOT) of the measuring sample is measured, and the measuring sample is gently sieved using a 12-mesh wire net, the mass (ON) of a powdered object of the measuring sample that has not passed the 12-mesh wire net due to blocking caused by moisture absorption is measured, and the vapor blocking ratio (%) is obtained according to the formula, Vapor blocking ratio (%)=ON×100 /TOT, when (c) the absorption ratio is measured as follows:
    1g of the water-absorbent resin powder is placed in a bag-form tea bag (10 cm×20 cm) made of a nylon textile having a sieve-opening of 57 micrometers (255-mesh), and the opening of the tea bag is heat sealed, next, 1 liter of 0.9 mass % saline solution is poured into a beaker having a capacity of 1 liter, and the tea bag is immersed therein for 1 hour, after the immersion, the tea bag is hung for 10 minutes to remove excessive water, and the total weight (F1) is measured, and as a blank, the weight (F0) of a tea bag not having placed therein the water-absorbent resin and having performed thereon the same operation is measured, the absorption ratio (g/g) of the water-absorbent resin powder is obtained according to the following formula, Absorption ratio (g/g)=(F1-F0)/Sample mass, when (d) the water retention amount is measured as follows:
    1g of the water-absorbent resin powder is placed in a bag-form tea bag (10 cm×20 cm) made of a nylon textile having a sieve-opening of 57 micrometers (255-mesh), and the opening of the tea bag is heat sealed, next, 1 liter of 0.9 mass % saline solution is poured into a beaker having a capacity of 1 liter, and the tea bag is immersed therein for 1 hour, after the immersion, the tea bag is hung for 10 minutes to remove excessive water, the tea bag obtained is placed in a basket type centrifugal dehydrator having a diameter of 30 cm, dehydrated at 1000 rpm (centrifugal force: 167 G) for 90 seconds, and then its total weight (R1) is measured, and as a blank, the weight (R0) of a tea bag not having placed therein the water-absorbent resin and having performed thereon the same operation is measured, the water retention amount (g/g) of the water-absorbent resin is obtained according to the formula, Water retention amount (g/g)=(R1-R0-Sample mass)/Sample mass.

2. The outer absorbent article combined with an inner absorbent article according to claim 1, wherein the absorbent body includes the water-absorbent resin powder satisfying the requirements of (a) to (d) on a skin surface side.

3. The outer absorbent article combined with an inner absorbent article according to claim 1, wherein an uppermost layer of the absorption layer includes the water-absorbent resin powder satisfying the requirements of (a) to (d).

4. The outer absorbent article combined with an inner absorbent article according to claim 1, wherein the outer absorbent article comprises a surface sheet material disposed on a skin surface side of the absorbent body and a liquid impermeable exterior sheet material disposed on an external surface side of the absorbent body, wherein at least one part of the surface sheet material is liquid permeable.

5. The outer absorbent article combined with an inner absorbent article according to claim 1, wherein the outer absorbent article is an open-type or pants-type diaper outer body.

6. An absorbent article comprising the outer absorbent article according to claim 1, wherein the inner absorbent article is attached to an inner side of the outer absorbent article.

7. The outer absorbent article combined with an inner absorbent article according to claim 2, wherein the outer absorbent article is an open-type or pants-type diaper outer body.

8. The outer absorbent article combined with an inner absorbent article according to claim 3, wherein the outer absorbent article is an open-type or pants-type diaper outer body.

9. The outer absorbent article combined with an inner absorbent article according to claim 4, wherein the outer absorbent article is an open-type or pants-type diaper outer body.

10. An absorbent article comprising the outer absorbent article according to claim 2, wherein the inner absorbent article is attached to an inner side of the outer absorbent article.

11. An absorbent article comprising the outer absorbent article according to claim 3, wherein the inner absorbent article is attached to an inner side of the outer absorbent article.

12. An absorbent article comprising the outer absorbent article according to claim 4, wherein the inner absorbent article is attached to an inner side of the outer absorbent article.

13. An outer absorbent article combined with an inner absorbent article, wherein the outer absorbent article comprises an absorbent body composed of at least one absorption layer, wherein the absorbent body includes a water-absorbent resin powder satisfying following requirements of (a) to (d):
    (a) Specific surface area measured by BET multipoint method: 0.040 m$^2$/g to 0.200 m$^2$/g,
    (b) Vapor blocking ratio: 0% to 0.90%,
    (c) Absorption ratio: 30 g/g to 70 g/g, and
    (d) Water retention amount: 32 g/g to 60 g/g;

when (b) the vapor blocking ratio is measured as follows:

10g of the water-absorbent resin powder is uniformly placed in a 5 cm-diameter plate made of aluminum, and left still for 2 hours in a constant temperature-and-humidity chamber of 50 degrees centigrade at a relative humidity of 80% RH, afterward the mass (TOT) of the measuring sample is measured, and the measuring sample is gently sieved using a 12-mesh wire net, the mass (ON) of a powdered object of the measuring sample that has not passed the 12-mesh wire net due to blocking caused by moisture absorption is measured, and the vapor blocking ratio (%) is obtained according to the formula, Vapor blocking ratio (%)=ON×100/TOT, when (c) the absorption ratio is measured as follows:

1g of the water-absorbent resin powder is placed in a bag-form tea bag (10 cm×20 cm) made of a nylon textile having a sieve-opening of 57 micrometers (255-mesh), and the opening of the tea bag is heat sealed, next, 1 liter of 0.9 mass % saline solution is poured into a beaker having a capacity of 1 liter, and the tea bag is immersed therein for 1 hour, after the immersion, the tea bag is hung for 10 minutes to remove excessive water, and the total weight (F1) is measured, and as a blank, the weight (F0) of a tea bag not having placed therein the water-absorbent resin and having performed thereon the same operation is measured, the absorption ratio (g/g) of the water-absorbent resin powder is obtained according to the following formula, Absorption ratio (g/g)=(F1−F0)/Sample mass, when (d) the water retention amount is measured as follows:

1g of the water-absorbent resin powder is placed in a bag-form tea bag (10 cm×20 cm) made of a nylon textile having a sieve-opening of 57 micrometers (255-mesh), and the opening of the tea bag is heat sealed, next, 1 liter of 0.9 mass % saline solution is poured into a beaker having a capacity of 1 liter, and the tea bag is immersed therein for 1 hour, after the immersion, the tea bag is hung for 10 minutes to remove excessive water, the tea bag obtained is placed in a basket type centrifugal dehydrator having a diameter of 30 cm, dehydrated at 1000rpm (centrifugal force: 167 G) for 90 seconds, and then its total weight (R1) is measured, and as a blank, the weight (R0) of a tea bag not having placed therein the water-absorbent resin and having performed thereon the same operation is measured, the water retention amount (g/g) of the water-absorbent resin is obtained according to the formula, Water retention amount (g/g)=(R1−R0−Sample mass)/Sample mass.

14. The outer absorbent article combined with an inner absorbent article according to claim 1, wherein the outer absorbent article is an adult diaper outer body.

15. The absorbent article according to claim 6, wherein the absorbent article is an adult diaper.

16. The absorbent article according to claim 15, wherein the inner absorbent article is a urine absorption pad.

17. The absorbent article according to claim 16, wherein (a) the specific surface area measured by BET multipoint method ranges from 0.103 $m^2$/g to 0.200 $m^2$/g.

18. The absorbent article according to claim 6, wherein (a) the specific surface area measured by BET multipoint method ranges from 0.103 $m^2$/g to 0.200 $m^2$/g.

19. The outer absorbent article combined with an inner absorbent article according to claim 13, wherein the outer absorbent article is an adult diaper outer body.

20. The outer absorbent article combined with an inner absorbent article according to claim 13, wherein (a) the specific surface area measured by BET multipoint method ranges from 0.103 $m^2$/g to 0.200 $m^2$/g.

\* \* \* \* \*